US012665075B2

(12) United States Patent
Harmon et al.

(10) Patent No.: US 12,665,075 B2
(45) Date of Patent: Jun. 23, 2026

(54) SYSTEMS AND METHODS FOR ANALYZING PATIENT DATA AND ALLOCATING MEDICAL RESOURCES

(71) Applicant: Iaso Automated Medical Systems, Inc., Decatur, GA (US)

(72) Inventors: Tyler Harmon, Auckland (NZ); LaDahvia Flounoy Fowler, Mableton, GA (US); Theodore Nicholson, III, Mableton, GA (US)

(73) Assignee: Iaso Automated Medical Systems, Inc., Decatur, GA (US)

( * ) Notice: Subject to any disclaimer, the term of this patent is extended or adjusted under 35 U.S.C. 154(b) by 264 days.

(21) Appl. No.: 17/679,596

(22) Filed: Feb. 24, 2022

(65) Prior Publication Data

US 2022/0277841 A1 Sep. 1, 2022

Related U.S. Application Data

(60) Provisional application No. 63/155,020, filed on Mar. 1, 2021.

(51) Int. Cl.
*G16H 40/20* (2018.01)
*G16H 10/60* (2018.01)
*G16H 50/30* (2018.01)

(52) U.S. Cl.
CPC ............. *G16H 40/20* (2018.01); *G16H 10/60* (2018.01); *G16H 50/30* (2018.01)

(58) Field of Classification Search
CPC ......... G16H 40/20; G16H 10/60; G16H 50/30
See application file for complete search history.

(56) References Cited

U.S. PATENT DOCUMENTS

| | | | |
|---|---|---|---|
| 8,184,854 B2 | 5/2012 | Bartsch | |
| 8,265,955 B2 | 9/2012 | Michelson et al. | |
| 10,299,689 B2 | 5/2019 | Ong et al. | |
| 10,339,653 B2 | 7/2019 | Gillies et al. | |
| 10,423,861 B2 | 9/2019 | Gao et al. | |

(Continued)

FOREIGN PATENT DOCUMENTS

| | | |
|---|---|---|
| AU | 2020101336 A4 | 8/2020 |
| AU | 2021103601 A4 | 8/2021 |

(Continued)

OTHER PUBLICATIONS

Singhal, L., Garg, Y., Yang, P., Tabaie, A., Wong, A. I., Akram, M., . . . Kamaleswaran, R. (2021). eARDS: A multi-center validation of an interpretable machine learning algorithm of early onset acute respiratory distress syndrome (ARDS) among critically ill adults with COVID-19. PLoS One (Year: 2021).*

(Continued)

*Primary Examiner* — Matthew L Hamilton
(74) *Attorney, Agent, or Firm* — Alan D. Minsk; FisherBroyles, LLP

(57) ABSTRACT

Systems, apparatuses, and methods for more efficiently allocating medical equipment and other resources (such as personnel, expertise, hospital space, etc.) to patients so that the equipment and resources are available when needed and before a patient's condition becomes urgent and life threatening or reaches a stage in the progression of a disease or illness that is no longer treatable with the available resources.

18 Claims, 7 Drawing Sheets

(56) References Cited

U.S. PATENT DOCUMENTS

| | | | |
|---|---|---|---|
| 10,452,813 B2 | 10/2019 | Sorenson et al. | |
| 10,665,346 B2 | 5/2020 | Baker | |
| 10,679,754 B2 | 6/2020 | Johnson et al. | |
| 10,813,580 B2 | 10/2020 | Dyell et al. | |
| 11,087,878 B2 | 8/2021 | Vesto et al. | |
| 2011/0015942 A1 | 1/2011 | Oakley et al. | |
| 2011/0119212 A1 | 5/2011 | De Bruin et al. | |
| 2013/0060549 A1 | 3/2013 | Grimes | |
| 2016/0203280 A1 | 7/2016 | Neville | |
| 2017/0049391 A1 | 2/2017 | Melker | |
| 2018/0068083 A1 | 3/2018 | Cohen et al. | |
| 2018/0070834 A1 | 3/2018 | Krauss et al. | |
| 2018/0071470 A1* | 3/2018 | Vairavan | A61M 16/0063 |
| 2018/0140252 A1 | 5/2018 | Luxon et al. | |
| 2018/0158552 A1 | 6/2018 | Liu et al. | |
| 2018/0322951 A1* | 11/2018 | Vairavan | G16H 50/20 |
| 2018/0330059 A1 | 11/2018 | Bates et al. | |
| 2019/0034590 A1 | 1/2019 | Oren et al. | |
| 2019/0108912 A1* | 4/2019 | Spurlock, III | C07K 16/2866 |
| 2019/0206564 A1 | 7/2019 | Shelton, IV et al. | |
| 2019/0391131 A1 | 12/2019 | Voros et al. | |
| 2020/0178903 A1* | 6/2020 | Chaudhuri | A61B 5/7445 |
| 2020/0211694 A1* | 7/2020 | Nye | G06T 7/11 |
| 2021/0022660 A1* | 1/2021 | Quinn | A61B 5/4842 |
| 2021/0063410 A1 | 3/2021 | Wilcox et al. | |
| 2021/0109110 A1 | 4/2021 | Eugen-Olsen et al. | |
| 2021/0151198 A1 | 5/2021 | Sabeti et al. | |
| 2021/0192727 A1* | 6/2021 | Ward | G06T 11/20 |
| 2021/0265028 A1 | 8/2021 | Cembrowski et al. | |
| 2021/0304898 A1 | 9/2021 | Otvos et al. | |
| 2021/0407648 A1* | 12/2021 | Ravishankar | G16H 50/20 |
| 2022/0238225 A1* | 7/2022 | Sieniek | G16H 40/67 |

FOREIGN PATENT DOCUMENTS

| | | |
|---|---|---|
| AU | 2021106628 A4 | 12/2021 |
| AU | 2021107097 A4 | 12/2021 |
| CN | 111681219 A | 9/2020 |
| CN | 111815608 A | 10/2020 |
| WO | 2019079166 A1 | 4/2019 |

OTHER PUBLICATIONS

Xu, W., Nan-Nan, S., Gao Hai-Nv, Zhi-Yuan, C., Yang, Y., Bin, J., & Ling-Ling, T. (2021). Risk factors analysis of COVID-19 patients with ARDS and prediction based on machine learning. Scientific Reports (Nature Publisher Group) (Year: 2021).*

Sidney Le, Emily Pellegrini, Abigail Green-Saxena, Charlotte Summers, Jana Hoffman, Jacob Calvert, Ritankar Das, Supervised machine learning for the early prediction of acute respiratory distress syndrome (ARDS), Journal of Critical Care, vol. 60, 2020, pp. 96-102 (Year: 2020).*

International Searching Authority of The PCT (US); "Notification of Transmittal of the International Search Report and the Written Opinion of the International Searching Authority, or the Declaration" dated Jun. 14, 2022; PCT Application No. PCT/US2022/017960; pp. 1-8 (2022).

European Patent Office; "Extended Search Report" dated Dec. 10, 2024; EP Application No. 22763815.2; pp. 1-12 (2024).

* cited by examiner

External Users of Patient Data

Patient Data for Training Models, Data Mining
109

Trained Models/ML Algorithms
110

Model Outputs
112

Pre-Processed Patient Data (Sorted, Anonymized for Training Data)
108

User Interface
116

Combined Risk Measure
114

RCCM Processes
106

Register Patient and Generate Identifier
102

Acquire Patient Data (Waveforms, Lab results, Images, etc.)
104

100

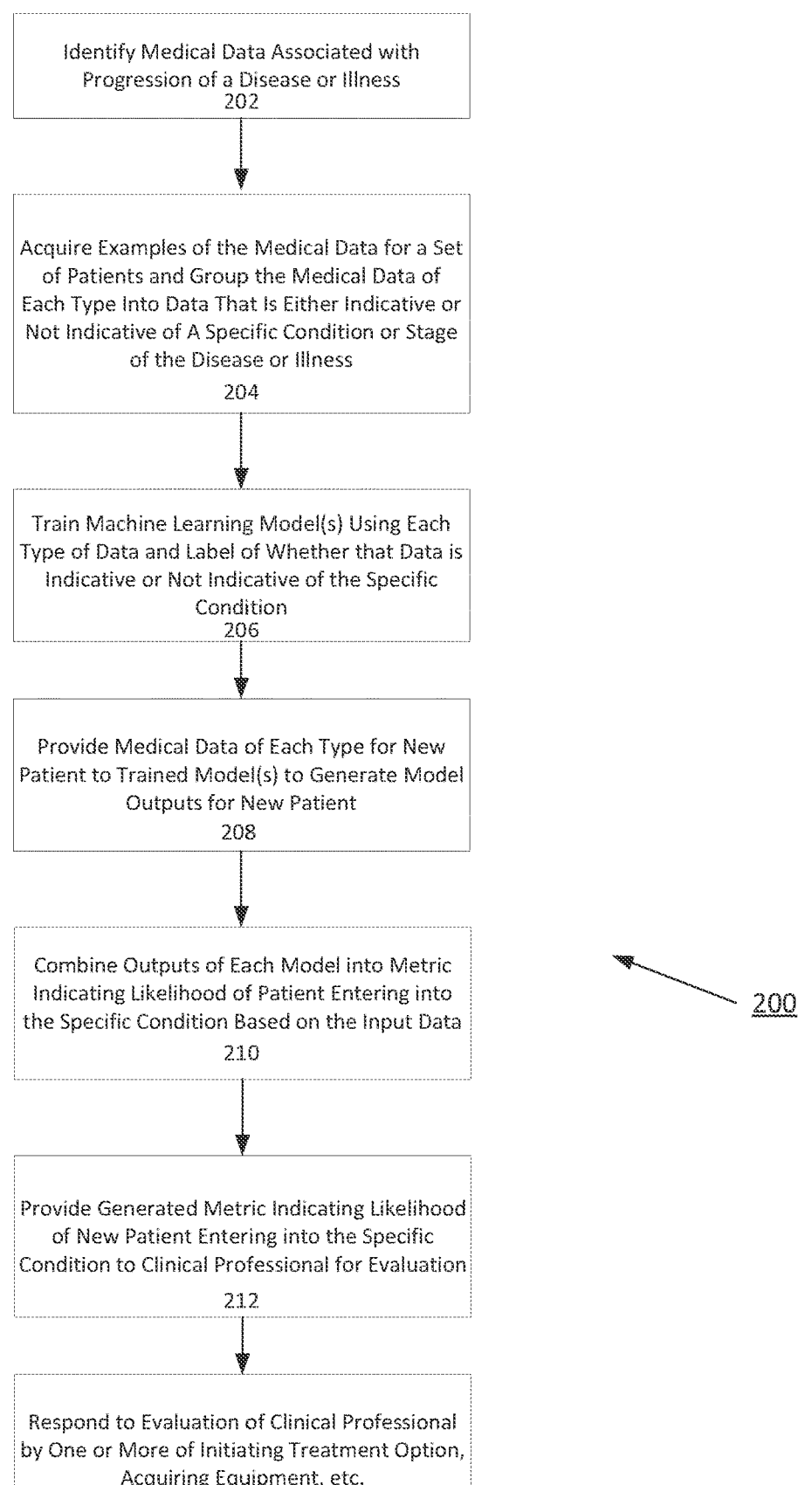

Identify Medical Data Associated with
Progression of a Disease or Illness
202

Acquire Examples of the Medical Data for a Set
of Patients and Group the Medical Data of
Each Type Into Data That Is Either Indicative or
Not Indicative of A Specific Condition or Stage
of the Disease or Illness
204

Train Machine Learning Model(s) Using Each
Type of Data and Label of Whether that Data is
Indicative or Not Indicative of the Specific
Condition
206

Provide Medical Data of Each Type for New
Patient to Trained Model(s) to Generate Model
Outputs for New Patient
208

Combine Outputs of Each Model into Metric
Indicating Likelihood of Patient Entering into
the Specific Condition Based on the Input Data
210

200

Provide Generated Metric Indicating Likelihood
of New Patient Entering into the Specific
Condition to Clinical Professional for Evaluation
212

Respond to Evaluation of Clinical Professional
by One or More of Initiating Treatment Option,
Acquiring Equipment, etc.
214

SYSTEMS AND METHODS FOR ANALYZING PATIENT DATA AND ALLOCATING MEDICAL RESOURCES

CROSS REFERENCE TO RELATED APPLICATION

This application claims the benefit of U.S. Provisional Application No. 63/155,020, entitled "Systems And Methods for Analyzing Patient Data and Allocating Medical Equipment," filed Mar. 1, 2021, the disclosure of which is incorporated, in its entirety (including the Appendix) by this reference.

BACKGROUND

In response to the global COVID-19 Pandemic, companies around the world are seeking to increase hospital capacity and the ability of healthcare systems to detect, triage, and treat victims of SARS-CoV-2. The bulk of these companies are seeking to increase this capacity by adding to the pool of equipment available to address the pandemic.

However, as is apparent by the hundreds of thousands of deaths experienced in the United States, the approach of simply making more equipment and faster, cannot properly address the needs of patients and healthcare providers. Further, these numbers do not include the 20-30% of people infected by COVID that will have symptoms longer than two to four weeks in "Long COVID" cases. Both the increased morbidity and the disabling long term health issues have impacted the healthcare system and the capability to deliver care to all patients. This is at least because the approach increasing the supply of equipment inherently ignores the resource allocation and distribution aspects of the problem. Experience has shown that when one seeks to increase the capacity of an established process (such as the availability of a resource), the increase can at most be only linear in nature if one is simply adding more input resources.

As a result, unless a pivot is made in the way capital medical equipment is designed, manufactured, distributed, and/or used, this bottleneck will continue to be a factor in thousands of deaths and increased severity of illness for those that survive. To change how these devices are designed requires years of engineering work; time that is not available during a growing and changing pandemic. Changing the manufacturing process requires years of engineering work, and an exponential increase in manpower and raw material for only a linear increase in output; these are resources, skilled labor, and time that are similarly not available during a pandemic.

Additionally, bottlenecks around intensive care staff, especially nurses and respiratory therapists, have emerged as causes of healthcare rationing in some areas (e.g., California, New York, and South Dakota) throughout the pandemic. These bottlenecks are equally difficult to solve by the linear addition of resources. This is especially impactful when there is little to no human resources to redistribute due to a lack of federal coordination and a universal demand on healthcare systems. Therefore, a solution that can exponentially increase the effectiveness and efficiency of human resources is equally critical to addressing this type of crisis.

Thus, systems and methods are needed to efficiently and effectively allocate medical and human resources to patients who need or will need specific equipment or expertise. In some embodiments, this is achieved by determining which patients are likely to need specific types of medical care and equipment in advance of their disease or condition progressing to a state in which that need is urgent, and the care or equipment may not be readily available. Embodiments of the invention are directed toward solving these and other problems individually and collectively.

SUMMARY

The terms "invention," "the invention," "this invention," "the present invention," "the present disclosure," or "the disclosure" as used herein are intended to refer broadly to all the subject matter described in this document, the drawings or figures, and to the claims. Statements containing these terms should be understood not to limit the subject matter described herein or to limit the meaning or scope of the claims. Embodiments covered by this disclosure are defined by the claims and not by this summary. This summary is a high-level overview of various aspects of the disclosure and introduces some of the concepts that are further described in the Detailed Description section below. This summary is not intended to identify key, essential or required features of the claimed subject matter, nor is it intended to be used in isolation to determine the scope of the claimed subject matter. The subject matter should be understood by reference to appropriate portions of the entire specification, to any or all figures or drawings, and to each claim.

Embodiments of the disclosure are directed to systems, apparatuses, and methods for more efficiently allocating medical equipment and other resources (such as personnel, expertise, hospital space, etc.) to patients so that the equipment and resources are available when needed and before a patient's condition becomes urgent and life threatening or reaches a stage in the progression of a disease or illness that is no longer treatable with the available resources.

In some embodiments, this is accomplished by a trained model or models that generate a "prediction" of whether a patient will enter a certain phase of a disease or illness. In response to this prediction, resources used to treat that phase of the disease or illness may be acquired, prepared for use, or otherwise made more readily available to use in treating the patient. The output of the trained model is a classification of the patient's condition as represented by the input data for the model, with the model generating an output representing a likelihood of the patient's condition progressing to a different phase. Based on this likelihood, a physician (or other clinical professional) may choose to request specific equipment or other resources and have those available for the patient in advance of the patient's condition entering the later phase. This preparation can enable more effective treatment of the patient and may serve to prevent an even more serious change in their condition.

In some embodiments, the model or models that are components of the disclosed system are trained machine learning models that evaluate or classify specific types of input data related to the medical condition of the patient. In some embodiments, the output of a plurality of models are combined into a metric or measure (referred to as a composite metric herein) that represents the likelihood of the patient's condition worsening and entering a specific phase of a disease or illness. In some embodiments, the generated metric or measure may be used by a medical professional to decide upon a treatment plan that correlates with the phase of the disease or illness. The treatment plan may also be used as an input for a medical equipment resource decision making process that allocates or reserves specific equipment or support staff for near-term use with more critical patients.

In some embodiments, the disease or illness being addressed by the resource allocation process is COVID-19

(SARS-CoV-2) and the input data to the model or models is comprised of (1) signal waveforms of one or more of EKG, SpO2, Respiratory Rate, and Blood Pressure, (2) lab results providing levels of specific markers (such as interleukins or D-dimers), and (3) images (such as x-rays) of the patient's lungs. In some embodiments, the metric or measure regarding the likelihood of the patient's condition worsening and entering a specific phase of the disease or illness is a "prediction" of the likelihood of the patient's condition entering into a situation of Acute Respiratory Distress Syndrome (ARDS).

In some embodiments and based at least in part on the generated metric or measure, a medical professional may decide upon a specific treatment for the patient prior to the patient entering the condition of ARDS. In some embodiments, the medical professional may request that certain equipment be made available in case it is urgently needed to treat the patient. In some embodiments, the equipment may be a non-invasive ventilator, invasive ventilator, nasal high flow apparatus, or ECMO (extracorporeal membrane oxygenation) machine.

In one embodiment, the disclosure is directed to a method for more efficiently allocating medical equipment and other resources to patients so that the equipment and resources are available when needed and before a patient's need becomes urgent and life threatening. In one embodiment, the method may include the following steps, stages, functions, processes, or operations:

> determining a current state of a medical condition of a patient;
>
> determining a likelihood of the patient entering a more severe state of the medical condition than the current state, wherein determining the likelihood of the patient entering a more severe state of the medical condition further comprises;
>
>> acquiring data characterizing the current state of the medical condition of the patient, the acquired data including at least two different types of data reflecting different techniques for assessing a condition of the patient;
>>
>> for each different type of data, inputting the data characterizing the current state of the medical condition of the patient into a model trained to output a metric representing a likelihood of the patient entering the more severe state of the medical condition based on the input data;
>
> combining the output of each model into a composite metric, the composite metric representing the likelihood of the patient condition entering the more severe state of the medical condition; and
>
> generating an output comprising the composite metric for evaluation by a medical professional, the composite metric used by the medical professional to determine whether to allocate a resource to treat the patient.

In one embodiment of the method, the acquired data comprises two or more of lab results, X-rays, ultrasound images, waveforms or signals indicating a state of the patient's organs or body functions, clinical observations, and psychological profile information. In one embodiment, the resource is an item of medical equipment, a staff member, a trained operator, a doctor, a nurse, a hospital bed, or another aspect of a hospital's capacity to treat patients.

In one embodiment, the illness or disease is a virus. In one embodiment, the virus is a coronavirus. In one embodiment, the coronavirus is COVID-19, and the resource is an extracorporeal membrane oxygenation (ECMO) machine.

In one embodiment, the disclosure is directed to a system for more efficiently allocating medical equipment and other resources to patients so that the equipment and resources are available when needed and before a patient's need becomes urgent and life threatening. The system may include a set of computer-executable instructions and an electronic processor or co-processors. When executed by the processor or co-processors, the instructions cause the processor or co-processors (or a device of which they are part) to perform a set of operations that implement an embodiment of the disclosed method or methods.

In one embodiment, the disclosure is directed to a set of computer-executable instructions, wherein when the set of instructions are executed by an electronic processor or co-processors, the processor or co-processors (or a device of which they are part) perform a set of operations that implement an embodiment of the disclosed method or methods.

In some embodiments, the systems and methods described herein provide analysis of patient medical data and recommended resource allocation services through a Software-as-a-Service (SaaS) or multi-tenant platform. The platform provides access to multiple users, each with a separate account and associated data storage. Each user account may correspond to a hospital or a group of clinical professionals, for example. Each account may access one or more services, an example of which are instantiated in their account, and which implement one or more of the methods or functions described.

Although portions of the systems and methods described herein are directed to treatment of a specific disease or illness (COVID-19) based on its progression in patients as indicated by specific medical data, this is for purposes of providing an example and the system and methods may be used to treat other illnesses and diseases. The mechanism of observation for these other conditions will, in some embodiments, focus on similar mechanical and image-based analysis of the disease or illness state of a given patient. For example, many zoonotic respiratory diseases have distinct mechanical features in heart performance, oxygen saturation, and lateral ground glass x-ray images. Some embodiments may be "tuned" to examine risk regarding these other conditions.

In some embodiments, the factors or features used to train the models were chosen (at least partially) because of their common appearance in chronic lung disease as well as novel zoonotic viruses. These types of viruses are expected to be continually increasing problems across the global healthcare landscape. In such use cases, the model or models used in embodiments will be trained using data that is associated with a phase or condition of the illness, with the phase or condition of a new patient being "predicted" by the trained model. When training a model, the training data may consist of data representing the condition of a patient with the phase or condition of the patient used as a label or annotation for the training data.

In some embodiments, the training data may include one or more types of data or data obtained from one or more techniques or sources, and the label may represent whether the patient's disease or illness became more severe over time. Such a trained model may be used to "predict" or provide an indication of whether a patient's condition will worsen given their current state as indicated by one or more types of relevant data (such as images, lab results, measures of a specific biomarker, etc.).

As mentioned, in some embodiments a plurality of trained models may be used with the outputs of the models representing a likelihood of a patient's condition worsening based on the data input to the model. The outputs of the plurality of models may be combined to generate a single metric representing the risk of the patient's condition worsening. The method of combining the outputs may itself be determined by a trained model, a rule-set, or may be additive, multiplicative, or a result of fitting values to a polynomial or other form of equation.

Other objects and advantages of the systems, apparatuses, and methods described will be apparent to one of ordinary skill in the art upon review of the detailed description and the included figures. Throughout the drawings, identical reference characters and descriptions indicate similar, but not necessarily identical, elements. While the exemplary embodiments described herein are susceptible to various modifications and alternative forms, specific embodiments have been shown by way of example in the drawings and will be described in detail herein. However, the exemplary embodiments described herein are not intended to be limited to the forms disclosed. Rather, the present disclosure covers all modifications, equivalents, and alternatives falling within the scope of the appended claims.

BRIEF DESCRIPTION OF THE DRAWINGS

Embodiments of the invention in accordance with the present disclosure will be described with reference to the drawings, in which:

FIG. 2 is a flowchart or flow diagram illustrating a general process for analyzing patient data and more efficiently allocating medical equipment and other resources to treat an illness or disease, in accordance with some embodiments;

DETAILED DESCRIPTION

Figure 1:
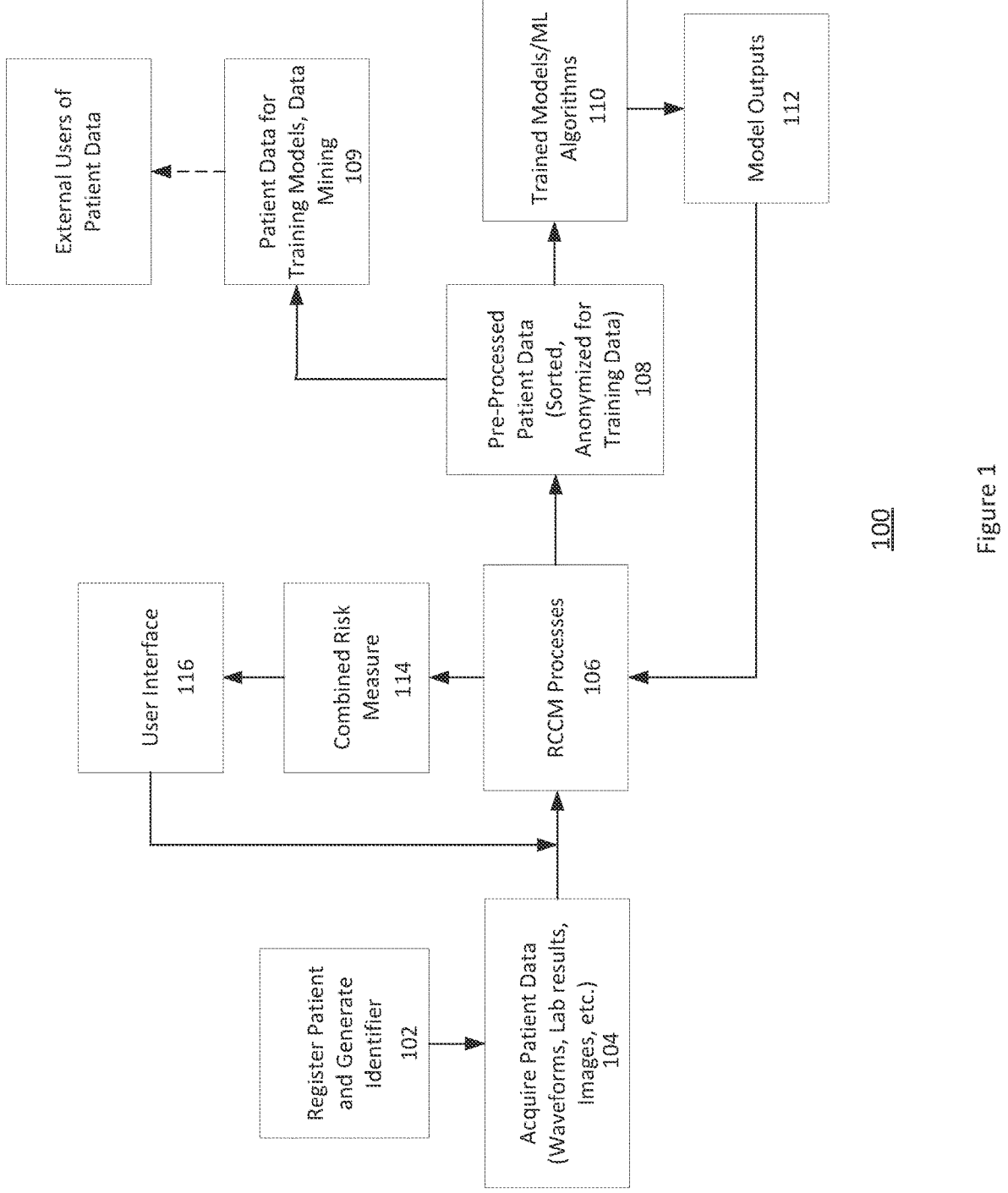
FIG. 1 is a diagram illustrating certain of the elements or components of a system for analyzing patient data and more efficiently allocating medical equipment and other resources, in accordance with some embodiments.

The subject matter of embodiments of the present disclosure is described herein with specificity to meet statutory requirements, but this description is not intended to limit the scope of the claims. The claimed subject matter may be embodied in other ways, may include different elements or steps, and may be used in conjunction with other existing or later developed technologies. This description should not be interpreted as implying any required order or arrangement among or between various steps or elements except when the order of individual steps or arrangement of elements is explicitly noted as being required.

Embodiments of the disclosure will be described more fully herein with reference to the accompanying drawings, which form a part hereof, and which show, by way of illustration, exemplary embodiments by which the invention may be practiced. The disclosure may, however, be embodied in different forms and should not be construed as limited to the embodiments set forth herein; rather, these embodiments are provided so that this disclosure will satisfy the statutory requirements and convey the scope of the disclosure to those skilled in the art.

Among other things, the present disclosure may be embodied in whole or in part as a system, as one or more methods, or as one or more devices. Embodiments of the disclosure may take the form of a hardware implemented embodiment, a software implemented embodiment, or an embodiment combining software and hardware aspects. For example, in some embodiments, one or more of the operations, functions, processes, or methods described herein may be implemented by one or more suitable processing elements (such as a processor, microprocessor, CPU, GPU, TPU, controller, etc.) that is part of a client device, server, network element, remote platform (such as a SaaS platform), or other form of computing or data processing system, device, or platform.

The processing element or elements may be programmed with a set of executable instructions (e.g., software instructions), where the instructions may be stored in a suitable non-transitory data storage element. In some embodiments, one or more of the operations, functions, processes, or methods described herein may be implemented by a specialized form of hardware, such as a programmable gate array, application specific integrated circuit (ASIC), or the like. Note that an embodiment of the inventive methods may be implemented in the form of an application, an application programing interface (API), a sub-routine that is part of a larger application, a "plug-in", an extension to the functionality of a data processing system or platform, or any other suitable form. The following detailed description is, therefore, not to be taken in a limiting sense.

Embodiments of the system, apparatuses, and methods disclosed and described herein enable a change to how critical medical equipment is allocated, routed, and used to treat patients. These embodiments leverage predictive analytics based on deep learning models to increase the capacity of hospitals and intensive care facilities by improving efficiencies in the allocation and availability of capital medical equipment (such as ventilators and extracorporeal membrane oxygenation machines), along with the human resources necessary to operate and effectively use the capital equipment (such as trained equipment operators, certified operators, nursing staff and doctors). In this way, the disclosed system and methods allow healthcare professionals to analyze risk signs and allocate resources in a more effective way.

In the context of the present disclosure, "resources" as used herein may refer to one or more of medical equipment, trained medical professionals (i.e., doctors, nurses, nurse practitioners), trained operators of the medical equipment, medications, hospital bed space, hospital emergency or intensive care space, etc. In some cases, once a resource is identified as likely being needed, this may also indicate a need for related or supporting resources. As an example, once a specific piece of medical equipment is indicated or predicted as being needed, this may generate a need for a trained operator, nurse, or staff member, supporting equipment, or other associated requirements.

As mentioned, although for purposes of providing an example, an embodiment of the disclosed system and methods is described in the context of providing medical care for a specific disease or illness (i.e., COVID-19 or one of its variants), the approach and techniques described may be applied to the treatment of other diseases, illnesses, or conditions. In treating a disease or illness other than COVID-19 (or its variants), the training data used, the trained models produced, the way the output(s) of the trained models are combined, and the interpretation of the combined outputs may differ from those described with reference to COVID-19.

In some embodiments, the system and/or methods may be implemented as a 3-module machine learning (ML) model or neural network for performing analysis of patient data and assisting in allocation of medical equipment by classifying a patient as more or less likely to be entering a phase of their illness in which they will need specific equipment. Each module or trained machine learning (ML) model is trained using data of a specific type or obtained from a specific process. The trained model or models are used to identify trends, features, and indicators (as a result of the classification of input data) as "live" data representing other patients is input to the system. The longer the system works in the field, the better the models/neural nets will be at predicting ARDS (or other state of a patient's illness or disease).

In some embodiments, the system comprises a plurality of models, with each module/ML model trained to evaluate or classify a different set of features (i.e., specific patient related data or measurements) to produce a value that is a factor of an overall risk calculation. In one example, the risk calculation is a model represented as an equation or set of equations that determine the probability of a patient going into ARDS, such as the second order derivative of an oxygen saturation curve, or the ratio between arterial blood gas and oxygen saturation.

In some embodiments, the probability may be based on a risk model that is weighted (or biased) towards providing as much notice as possible before a patient goes into ARDS (or other state of concern). In a typical use case or scenario, the risk model will not make decisions on behalf of the clinicians, but instead will provide them with as much data and information as feasible. In some embodiments, that data or information may be condensed into a single indicator or metric (in some cases, more than a single indicator or metric) that they can leverage to make faster and better lifesaving decisions in the ICU. A risk model will typically be examined by clinicians in parallel to its development to ensure that it represents both a practical and an accurate model of the factors that contribute to a patient going into ARDS (or other conditions that the ML models have been trained to evaluate) and can assist in providing the best possible patient outcomes.

In some embodiments, one module or ML model will examine X-Ray data to predict the severity of the disease manifestation in a patient's lungs. This concept has been used in the diagnosis of COVID-19, but not in determinations of the severity of the disease's impact or disease progression for a patient. Another module or ML model will examine respiratory and cardiovascular data currently collected for ICU patients. A third module or ML model will analyze lab panels to predict risk of ARDS. In one embodiment, the risk model will combine each ML model output and calculate a value that can be leveraged by clinical professionals (e.g., doctors, nurses, or other suitable medical professional) with minimal training with the tool. Other combinations of the number of trained models, the specific data being evaluated by a trained model, and the methodology of combining the outputs of the trained models are possible and fall within the description provided by this disclosure.

In some embodiments, a set of components, elements, or functional modules of an example system may include:

Risk Compilation and Communication Module (RCCM): this module functions as an intermediary between the three (or however many are used) machine learning models and the users. The module takes as inputs the risk measures or metrics output by the three trained machine learning models or modules and uses them to determine or calculate the patient's risk of going into ARDS;

In some embodiments, the RCCM may modify the ML model outputs based on subprocess variables, such as time since admission to a hospital, date of diagnosis with COVID-19, type of COVID test administered (as PCR versus antigen tests may influence the certainty with which a diagnosis can be analyzed), identified variants of SARS-CoV-2 (the 69/70 S dropout variant B.1.1.7 would indicate that non-invasive ventilators or other types of therapies generating droplet output should not be used), intake vitals, current vitals, trending data parameters, or other such inputs;

The modification to the output generated by a ML model may take the form of an additive or subtractive factor, a multiplicative or scaling factor, a rule that determines whether a factor will be considered when generating a final metric, etc.;

In some embodiments, additional data may be collected and used as an input to a trained ML model, rule-set, formula, heuristic, or other resource allocation process, where such data may include staffing numbers, certifications or information indicative of the training of medical staff, hospital capacity and occupancy, available power, etc.

In some deployment architectures, the RCCM module can serve as the point of contact between both the user (such as a physician or other clinical professional) and the data source(s) for the three ML models. Because it may act as a data intake and distribution node, the RCCM module may require the most processing power and fastest data transfer connection between the data source, users, and ML model modules;

Lab Results Module: this model or module may include the algorithmic capabilities of a deep learning or machine learning model used to take in data from the lab testing results of a patient and generate an output reflecting the risk or likelihood of the patient entering a worse condition based on the input data. In some embodiments, the model may consider specific markers, or a combination of specific markers, such as interleukins or D-dimers;

A set of training data including these inputs may be used to train a model and similar data not used for training may be used as part of a continual updating and refinement of the model as more data is collected. In some embodiments, the training data and model updating process may be separate from the dynamic (i.e., real-time patient data) data being input to a current model;

An architecture in which the training data is partitioned from the "live" input data structures is beneficial to deep learning as an engineering instrument, as well as to ensure compliance with software development standards (such as IEC 62304, IEC 82304 and 80002-2, or other relevant standard or requirement). This architecture design is used for all 3 deep or machine learning model modules that provide risk parameter metrics to the RCCM;

In some embodiments, the lab results module may output a risk score, measure, metric, or value for a factor in a risk calculation based on the inputs, with that score or value communicated to the RCCM over a network;

Note that in some embodiments, other data or information may be used in addition to, or instead of the specific data mentioned. For example, information or data related to pre-existing conditions may be included as training data for the same or a separate model, with that information or data being used as a contribution to a patient's risk of entering a more serious phase of an illness or disease;

An example of a data flow and module arrangement for an implementation of an embodiment of the disclosed system or platform configuration is represented in FIG. 1, which is a diagram illustrating certain of the elements or components of a system for analyzing patient data and more efficiently allocating medical equipment and other resources, in accordance with some embodiments;

In some embodiments, at least one configuration of the lab results module will weight the outputs of the module to be zero during an initial check-in period of a patient into the intensive care unit so that other risk variables will not be influenced, and risk scores can be calculated unbiased by the timing or availability of the lab results;

Cardio-Respiratory Module: this machine learning model or module will receive raw waveform data for one or more of a patient's EKG, SpO2, Respiratory Rate, Heart rate, and Blood Pressure. These waveforms may be input to the RCCM asynchronously to not create a dependency on the timestamps for input data;

Synchronous calculations would require timestamp matching between patient monitoring systems that embodiments would need to interface with, as well as with the RCCM or intermediary systems. By implementing asynchronous capabilities, data can be acquired dynamically, and aliasing errors can be smoothed via interpolation of data and filtering mechanisms;

An asynchronous approach may require greater processing power and programming complexity but will reduce error in the accuracy of the risk scores generated and in the risk exposure to the patient. Therefore, an asynchronous approach may act as a risk control to limit potential harm due to missed data points that could arise from a requirement of synchronized data acquisition;

The asynchronous waveforms are processed by the Cardio-Respiratory Module with risk factors generated from a waveform being weighted and compiled into a multi-dimensional variable and output to a client user interface through the RCCM. As an example, the multi-dimensional variable may take the form of a single weighted equation such as (3*Oxygen Saturation+2*Heart Rate . . . etc.) or in another embodiment, may take the form of a system of equations represented as a matrix. By leveraging multi-dimensional variables instead of a simple additive measurement, more complex calculations can be performed by the model, allowing for more accuracy in the model via higher precision;

For example, some of the data processing steps disclosed would be unable to be performed by clinical professionals in sufficiently rapid fashion given the higher-level math and computational power required for transforms of large data sets and trends;

As an example, in one embodiment, the disclosed data processing may utilize multiple linear and nonlinear transformations of single data points and trending data simultaneously to generate predicted outcomes for a given patient;

To generate a risk score from an individual waveform, it is desirable to identify or overlay the input waveform with the most similar waveform of the set of training data waveforms. To facilitate this, the training data for this model/module may include each artifact of an expected cycle for each waveform type.

For example, if an asynchronous waveform contains a QT complex in an EKG, then use of the waveform to train a model will include identifying a "matching" EKG. Pattern matching algorithms may be applied to training data as a part of the model training process so that artifacts are recognized as the models are trained;

In one embodiment, a configuration of this module or model will include a baseline set of waveform artifacts pre-programmed to assist the training process for early iterations. This will act as a risk control for initial patients so that normal waveform artifacts do not contribute arbitrarily to the risk score variables output to the RCCM. Other configurations may include a filtering mechanism within the RCCM, for example;

Sampling or filtering as applied to asynchronous waveforms may depend on the risk scores of the patient at a given time. For example, lower risk patients may have aggressors that are milder and observed over longer time periods. Higher risk patients may require higher sampling frequencies to ensure that the risk measure is as accurate and useful as possible. Processing involving training data may be leveraged so that risk of rapid patient decline contributing to missed risk increases is minimized. Similarly, aggressive escalation protocols may be implemented initially so that a lack of training data does not contribute to the probability of a hazardous situation in which the patient has an increased risk profile that is not reflected by the system;

Imaging Module: this model or module receives raw lung x-ray image data from the RCCM as an input and analyzes it, based on a set of training data consisting of images of patient lungs of varying severity of COVID-19 (in this example embodiment) progression;

In some embodiments, this module will initially isolate the outline of the lungs to minimize the use of static memory for image storage as a control measure for the infrastructure on which the module will be executed;

Once the lung boundary is identified or drawn, the internal structures of the lung will be analyzed for progressive markers of the disease, such as (for the example of COVID-19) ground glass bilateral pneumonia, severity of bacterial pneumonia, inflammation, and clotting. Each of these phases (or other phases discovered during the training of the module), may be used as inputs into the risk score equation;

In some embodiments, the risk score equation will produce multi-dimensional variable outputs to the RCCM, which may be processed within that model, and be presented to the client user interface. As with the Cardio-Respiratory Module, certain known artifacts may be pre-programmed aggressors to lower the risk of a situation in which a low volume of training data contributes to a hazardous situation. Overtime, these artifacts may be added to or subtracted from as the model is refined via deep learning and the acquisition of more patient data.

One benefit of the processing pipeline that results in the overall risk (or likelihood of a worsening of the patient condition) metric or measure is to condense the collected patient information into something more easily digestible and actionable by a medical professional, given the realities of patient care under time constraints and difficult conditions. Physicians and other clinical professionals may not benefit from another chart to digest or train on; rather, they need reliable and actionable information.

In some embodiments, the system or platform may comprise a cloud-based architecture (e.g., Software-as-a-Service or a multi-tenant platform) to result in minimal requirements for new infrastructure and reduce the burden on existing hospital information and data processing systems. By leveraging this design, the system will be able to provide benefits with the least disruption to existing systems and internal hospital (or physician office) data processing and data storage architectures. In general, a configuration or implementation of an embodiment of the system and methods described may involve features that improve interoperability with an existing system (such as a hospital or medical provider data or IT system) and ensure the security of data during transfer and processing of data between existing systems and the system and methods described.

The disclosed system and data processing flow can be implemented in multiple ways and as part of (or integrated with) one or more existing infrastructures, architectures, settings, and operational environments. Below are descriptions of several non-limiting examples of such possible configurations.

Configuration 1.1: This configuration is one in which all four modules (the RCCM and the three trained machine learning models) reside in a cloud-based environment with minimal (if any) infrastructure within a hospital setting. In this configuration, data is passed to the system via a browser-based client that is integrated with a desktop on which the client is run. Each node or processing cluster for each of the trained models or modules will be isolated from one another and connect to the RCCM and the appropriate databases or data sources. The desktop client will act as the graphical user interface (GUI) through which a healthcare worker can view the risk measure or measures, and in some cases the patient data. The connection to the private, validated cloud environment of the RCCM will leverage an industry standard in-hospital HL7 (or similar) protocol for compatibility to meet or exceed existing cybersecurity requirements, and to ensure data integrity.

Configuration 1.2: This configuration is similar to that of configuration 1.1 except that data will be passed from the desktop-based program, through the hospital internal network to a server on which the RCCM will execute. The RCCM server will communicate over TCP protocols to the external trained models or modules which will reside in a validated cloud environment. In this configuration, as with others, the data will be encrypted at rest and in transit to maintain data integrity throughout the data pathways.

Configuration 1.3: This configuration will be similar to that of configuration 1.2 except that only the database components (i.e., the data storage elements) of each module will reside in a validated cloud environment. The RCCM and each trained model or module will reside in isolated servers that communicate centrally over CAT6 standard cabling and a network switch to the RCCM server. This will centralize the computational resources in the hospital's network. Outbound communication to the database components will occur over a TCP protocol. The outbound communication and internal communications may operate as part of a zero-trust architecture to confirm data integrity at each point of contact within the configuration (as with one or more of the previous configurations).

Configuration 1.4: This configuration is similar to that of configuration 1.3 except that client to RCCM communications take place over a UDP protocol (or similar transport protocol that provides speed for time-sensitive data transfers) and therefore require greater network management resources within the RCCM.

Configuration 1.5: This configuration is similar to that of configuration 1.2 except that the communication between the desktop client and the RCCM occurs over UDP and outbound communications to the cloud-based modules also occurs over UDP.

Configuration 1.6: This configuration is similar to that of configuration 1.5 except outbound communications to the cloud-based modules occur over TCP.

The following provides a further description of the operation of each trained machine learning (ML) model, with a description of the input data, the annotations or labels, how the trained model generates a classification (a risk assessment) based on patient data, and how the output of a model is used:

In the example of using the disclosed system and methods to assist physicians and other clinical professionals treating patients with COVID, the output of the data processing pipeline is a value that represents a risk score or prediction of whether a patient is likely to go into ARDS;

In some embodiments, this may be represented as a single number calculated from a regression equation that includes the outputs of each ML model or module and combined based on weights derived from the training data. Training data categories (that is types of data or sources of data) that have a higher positive predictive value correlation with a success outcome (e.g., if oxygen saturation is much more indicative of entering ARDS than heart rate) may be assigned a higher weighting in the overall risk calculation;

The training data for each machine learning model varies, depending upon the purpose of the model and the type of patient data it is processing or evaluating:

The Cardio-Respiratory module may be trained using waveforms for one or more of Blood Pressure, EKG, SpO2, and Heart Rate (in the form of a tachogram or another suitable format);

The Lab Data Module may be trained using one or more of D-Dimer, Interleukin 6 and Interleukin 8, or other such monokines and inflammatory indicators (such as monokine induced by interferon gamma and other cytokines) of lung condition;

The Imaging Module may be trained using X-Ray and/or CT scan data and be trained to identify specific artifacts, such as the presence of bilateral "ground glass" scarring of alveoli;

Each model is trained based on the specific training data and an annotation or label indicating whether that set of patient data was associated with a patient that went into a condition of ARDS or not. In one embodiment, the output of each model is a measure (typically expressed as a number within a range of [0,1]) representing the likelihood of a patient having that input data going into ARDS;

As mentioned, each data group will be labeled (annotated or tagged) as either ARDS or non-ARDS in an initial implementation. Each waveform will receive its own tag, lab outputs will receive a grouped tag (e.g., results from a patient that is tagged as ARDS will be tagged as being associated with ARDS whereas other data types will be tagged individually), and each image will receive a tag;

In some embodiments, the outputs of the three machine learning models may be combined into a risk measure or prediction of the patient going into ARDS. The combination may be a weighted combination of the three factors (with, for example, the lab results initially assigned a weight of zero within the final output equation calculated in the RCCM, until at least 24 hours after the patient is checked into the ICU/COVID-ward, as this is the standard processing time and should not be a factor in determining a patient's initial risk);

For Waveforms in the Cardio-Respiratory Module, time matching may be implemented as packets come in from the data source. The data could be sourced from the electronic health record (EHR) system of the hospital and obtained from the patient monitoring equipment itself. The packets will be matched as best they can to a check-in time that starts at zero when the patient is checked into the ICU. The waveform input will be tagged with a timestamp. The model or module will attempt to match the timestamp with the training data timestamps and compare it against the ARDS and non-ARDS models;

Matching is performed to identify the data inputs with model variables that are associated with a similar time since patient admission. This enables the model to analyze waveforms for artifacts, such as decay in the oxygen saturation value over time, and enables the system to create a facsimile of synchronous calculations via an asynchronous approach;

For example, if a patient has been waiting in the Emergency Department for two days, their data needs to be matched with a two-day timepoint in the data models. Otherwise, the patient's decline relative to time of diagnosis will not be as accurately matched with variables that are time dependent or show large changes over time;

In one embodiment, a regression calculation may be performed, and an R-squared or similar value generated. The types of waveforms may be weighted based on their criticality to the equation; for instance, SpO2 may be weighted exponentially, while Blood Pressure may be weighted linearly. This will produce a risk score of the probability of a patient entering a condition of ARDS;

A similar exercise may be performed based on variance between the lab data inputs for a patient and the ARDS tagged data used to train the model. As the variance between the input data and the ARDS tagged data decreases, the risk score will increase for that module;

As imaging data is entered into the Imaging Module, the system may operate to first identify or isolate the lungs within the image. After that, a pixel percentage match to the ARDS tagged image model may be calculated. The Imaging module may determine a pixel matching percentage with the trained ARDS tagged images within the drawn boundary of the lungs on the X-Ray;

Once the three (3) risk metrics or values (one risk score or metric from each trained model) are calculated and weighted for time within the ICU (or another relevant event or start point), they are combined to produce a likelihood of the patient entering ARDS (because each risk metric is a dependent variable within the larger regression of the ARDS determining module—the RCCM module);

Time-based weighting is important because the time at which data is collected from a patient (relative to when they entered the hospital, the ICU, etc.) can impact the risk measures derived from factors that are dependent on time. For example, if blood oxygen saturation is high, and the patient has been under observation for 3 days, it may be unlikely that invasive ventilation is an appropriate intervention. Conversely, if a patient has just arrived in the ICU and already has a high value in the derivative of their oxygen saturation curve, then even if the value is relatively high, this patient may be at a much higher risk for ARDS than would otherwise be determined;

As described, in the context of treating patients with COVID, the system will output a probability or likelihood of whether a patient is likely to enter ARDS, expressed as a score, value, or composite metric. The output value allows clinical professionals to quickly make decisions regarding patient risk and initiate actions to decrease that risk. In some embodiments, the system may be able to make suggestions to clinical professionals regarding a course of action or treatment plan (note that this is not intended to be a diagnostic tool, but instead a potential learning mechanism for which treatment approach would most likely improve a patient outcome).

FIG. 1 is a diagram illustrating certain of the elements, components, or processes of a system 100 for analyzing patient data and more efficiently allocating medical equipment and other resources, in accordance with some embodiments. With reference to the diagram, the elements, components, or processes that implemented by an embodiment of system 100 may comprise the following:

A patient profile is created and each set of raw data for that patient is tagged with a unique identifier either generated by the system or acquired from the EHR system. The identifier is associated with all the raw data structures as a tag through the data processing flow (as suggested by process 102);

Raw data in the form of one or more of waveforms, lab values, and images are acquired for the patient (as suggested by process 104);

The acquired patient data is transferred to the RCCM component (element or component 106) using the installed configuration—the RCCM operates to sort the received data and direct it to the correct module. The RCCM may also apply a timestamp to the waveform data packets, as these may be broken down into sets of data versus time to be re-formed into waveforms in the Cardio-Respiratory Module;

1. In some embodiments, the acquired data may be pre-processed, either within the RCCM or another component. The pre-processing may include the sorting described and in the case of preparing data for use in training a model, it may include anony-mizing some or all the data (as suggested by element 108);

2. Anonymized patient data may be provided to a database or data storage element (as suggested by element 109) for use in training and/or updating the models;

A. In some embodiments, this data may be "mined" to develop separate data sets for use in other models and/or to segment patients for purposes of specific investigations, etc.;

Each trained ML module performs the classification operation described and outputs an associated metric or value (as suggested by elements or processes 110 and 112);

The outputs of the individual trained models are provided to the RCCM 106 which performs the determination of a composite risk score (element 114) for a patient;

The risk score 114 may then be displayed by a user facing graphical user interface (element 116) for use by the clinical staff;

Once an outcome for the patient is determined, it is entered into the system via raw data from the EHR system or from the graphical user interface 116. The patient data and outcome are passed to the RCCM 106, which removes the patient identifier and applies an ARDS or non-ARDS tag to the patient dataset. This data is then added to the training database 109 and may be used to update the machine learning models without compromising patient privacy.

FIG. 2 is a flowchart or flow diagram illustrating a method or set of processes 200 for analyzing patient data and more efficiently allocating medical equipment and other resources, in accordance with some embodiments. As shown in the figure, these processes, operations, or functions may include:

At stage or step 202, Identifying The Types Or Categories Of Medical Data Associated With The Progression Of A Specific Disease Or Illness;

these represent types of patient related data (patient characteristics, measurements, other factors or indi-cators) that have been found useful in tracking the progression of a specific disease or illness, and may include clinical or psychological observations;

the factors or indicators may be learned or provided by expert analysis of multiple cases and how a disease or illness progresses in patients;

examples of such factors or indicators may include but are not limited to lab results for specific markers, X-ray, ultrasound or other images, wave-forms/signals indicating a state of an organ or body function, clinical observations, or psycho-logical profiles;

At stage or step 204, Acquiring Examples Of The Types Of Medical Data For A Set Of Patients And Grouping The Medical Data Of Each Type Into Data That Is Either Indicative Or Not Indicative Of A Specific Condition Or Stage Of The Disease Or Illness (such as a point at which their condition worsens, or a type of treatment is needed);

This may include associating available data of various types (images, waveforms, lab results, etc.) into groups, with one group indicating a condition and one group not indicating the condition;

At stage or step 206, Train a Separate Machine Learning Model Using Each Type of Data and a Label of Whether that Data is Indicative or Not Indicative of the Specific Condition;

This involves training one ML model for each data type with an associated label or annotation indicating whether the example of data is indicative or not of the condition;

At stage or step 208, Provide Medical Data of Each Type for a New Patient to the Trained Model(s) to Generate Model Outputs for the New Patient;

At step or stage 210, Combine the Outputs of Each Model into a Composite Metric or Value Indicating the Like-lihood (such as the overall probability) of the Patient Entering into the Specific Condition Based on the Input Data for that Patient;

the composite metric may be formed from one or more of a weighted sum of the output of each model, a fit of the outputs to a polynomial or other function, a dynamically varying function of time that provides greater weighting based on the time since an event (such as entry to a hospital or ICU) and/or when specific data was collected—the contributions of each model output to the combined metric or the method of combination may be dynamically altered as a patient's treatment progresses;

At stage or step 212, Provide the Generated Metric Indicating the Likelihood of the New Patient Entering into the Specific Condition to a Medical Professional for Evaluation;

this may include generating an alert or notification on a user interface or generating a message to a medical services provider if the patient's condition has rap-idly worsened or is expected to (e.g., because the value of the metric has changed more quickly than expected, because the value of the metric has reached a critical level, etc.); and if desired At step or stage 214, Respond to the Evaluation of the Medical Professional by One or More of Initiating a Treatment Option, Acquiring Specific Equipment, etc. (this is optional and depends on the configuration of the system and its integration with user systems for gen-erating alerts, requesting resources, etc.).

Figure 3:
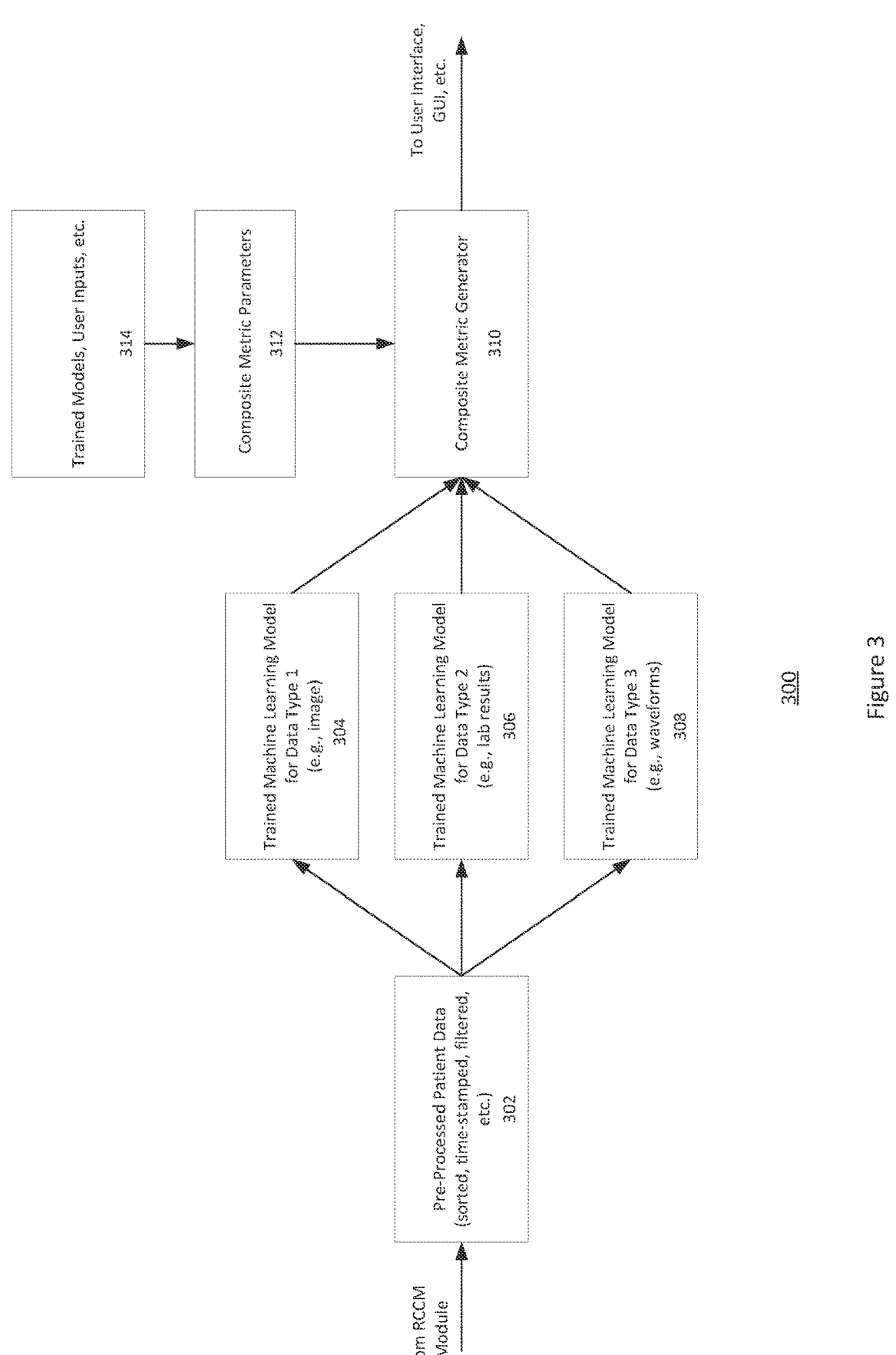
FIG. 3 is a diagram illustrating an example of a processing flow for generating a composite metric representing a likelihood of a patient entering a worse state of a diseases or illness, in accordance with some embodiments.

FIG. 3 is a diagram illustrating an example of a processing flow 300 for generating a composite metric representing a likelihood of a patient entering a worse state of a disease or illness, in accordance with some embodiments. The diagram illustrates a processing flow based on the use of three (3) types or sources of data, with each type or source associated with a trained model. If a greater or lesser number of data types (for example, only images and waveforms) are used, then the number of trained models will be increased or reduced accordingly.

As shown in the figure, processing flow 300 comprises a source or sources of patient data, represented in the figure by the "From RCCM Module" input to the pre-processing operations 302. Pre-processing operations 302 receives patient data from a control module (e.g., the RCCM in some embodiments) or other source(s) and in response performs one or more operations on the data to prepare it for distri-bution to the appropriate trained model. In some embodi-ments, the pre-processing and distribution operations may be performed by the RCCM.

In some embodiments, the pre-processing operations may comprise one or more of:

Sorting input patient data into categories of data types (images, waveforms, etc.);

Time-stamping elements of the input or sorted data;

Filtering, thresholding, or otherwise selecting data;

Anonymizing the data for use in training a model.

The pre-processed data is then transferred or distributed to the appropriate trained model, with one trained model being used to classify or evaluate each type of data. In the example illustrated, there are three trained models (304, 306, 308), with each trained model configured to receive a data type (referred to as Data Type 1, Data Type 2, and Data Type 3 in the figure) and in response generate a measure of the likelihood that a patient associated with that data type will enter a more severe state of their disease or illness. The output of each trained model may be a number (e.g., between zero and one), binary value, flag, or other indicia. The outputs from each trained model are provided to a Composite Metric Generator process or element 310.

Composite Metric Generator process or element 310 operates to combine the outputs from each of the trained models into an overall measure of the likelihood that the patient will enter a more severe state of their disease or illness. As described herein, this process of combining the outputs of the trained models may include, but is not limited to or required to include one or more of:

Weighting each of the trained model outputs prior to combining them;

Adding, multiplying, or exponentiating one or more of the outputs;

Fitting the trained model outputs to a formula, equation, or curve;

Applying a threshold process or filtering the outputs; and

Analyzing the individual metrics in view of the outputs from trained models within and in-between the modules.

The weights, rules, formulas, or other factors used to generate the composite metric may be provided by a separate process, illustrated as Composite Metric Parameters 312 in the figure. Composite Metric Parameters 312 may represent a process to generate inputs to Composite Metric Generator process or element 310 based on another process or inputs (such as that suggested by process or element 314 in the figure (i.e., Trained Models, User Inputs, etc.). Composite Metric Parameters 312 may take the form of a rule-set, heuristic, formula, threshold operation, filter operation, set of weights, set of exponents, or other similar information. The rule-set, heuristic, formula, threshold operation, filter operation, set of weights, or set of exponents may be generated by a user, a separate trained model, or other source 314.

The output of Composite Metric Generator processor element 310 is provided to a user interface, GUI, user device application, or other process, component, or element for presentation to a medical professional. The value of the composite metric (or its change over time) may cause an alert to be generated or message sent to the medical professional to assist in monitoring the patient's condition. The value of the composite metric (or its change over time) may be used by the medical professional to decide whether a specific item of equipment may be needed, a bed in the ICU reserved, or other action taken to assist the patient.

Figure 4:
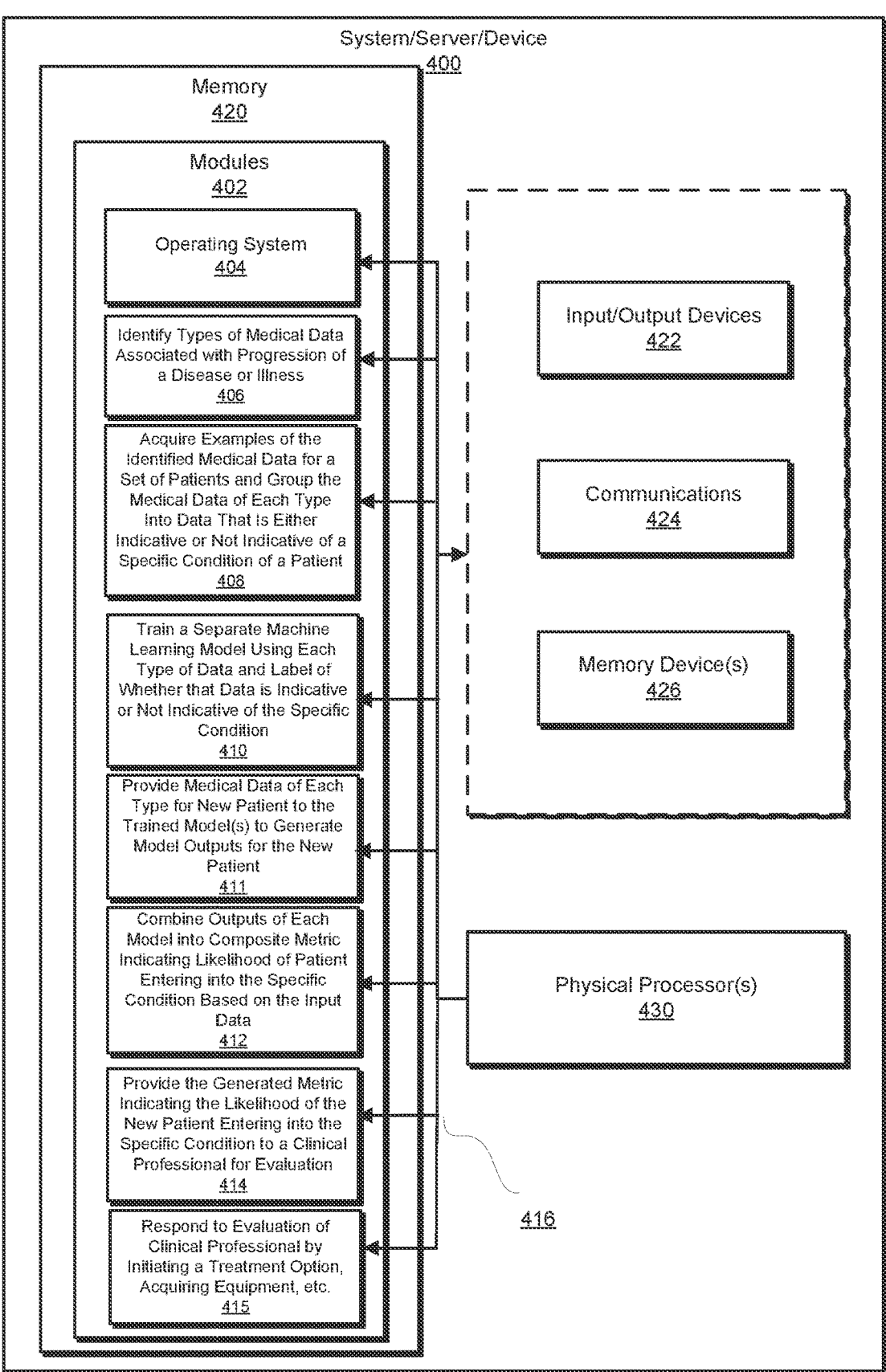
FIG. 4 is a diagram illustrating elements or components that may be present in a computer device, server, or system configured to implement a method, process, function, or operation in accordance with some embodiments of the invention.

FIG. 4 is a diagram illustrating elements or components that may be present in a computer device, server, or system 400 configured to implement a method, process, function, or operation in accordance with some embodiments of the invention. As noted, in some embodiments, the inventive system and methods may be implemented in the form of an apparatus that includes a processing element and a set of executable instructions. The executable instructions may be part of a software application and arranged into a software architecture. In general, an embodiment of the invention may be implemented using a set of software instructions that are designed to be executed by a suitably programmed processing element (such as a GPU, TPU, CPU, microprocessor, processor, controller, computing device, etc.). In a complex application or system such instructions are typically arranged into "modules" with each such module typically performing a specific task, process, function, or operation. The entire set of modules may be controlled or coordinated in their operation by an operating system (OS) or other form of organizational platform.

System 400 may represent a server or other form of computing or data processing device. Modules 402 each contain a set of executable instructions, where when the set of instructions is executed by a suitable electronic processor (such as that indicated in the figure by "Physical Processor(s) 430"), system (or server or device) 400 operates to perform a specific process, operation, function, or method. Modules 402 are stored in a memory 420, which typically includes an Operating System module 404 that contains instructions used (among other functions) to access and control the execution of the instructions contained in other modules. The modules 402 in memory 420 are accessed for purposes of transferring data and executing instructions by use of a "bus" or communications line 416, which also serves to permit processor(s) 430 to communicate with the modules for purposes of accessing and executing a set of instructions. Bus or communications line 416 also permits processor(s) 430 to interact with other elements of system 400, such as input or output devices 422, communications elements 424 for exchanging data and information with devices external to system 400, and additional memory devices 426.

As shown in the figure, modules 402 may contain one or more sets of instructions for performing a method or function described with reference to the Figures, the descriptions of the functions and operations provided in the specification, and the Appendix. These modules may include those illustrated but may also include a greater number or fewer number than those illustrated. The computer-executable instructions that are contained in the modules or in a specific module may be executed by the same processor or by different processors. For example, the computer-executable instructions that are contained in a single module may be executed (in whole or in part) by one processor or by more than one processor. For example, certain of the operations or functions performed as a result of the execution of the instructions contained in a module may be the result of one or more of a client device, backend device, or a server executing the instructions. Thus, although FIG. 4 illustrates a set of modules which, when considered together, perform multiple functions or operations, these functions or operations may be performed by different devices or system elements, with certain of the modules (or instructions contained in those modules) being associated with those devices or system elements.

The application modules and/or sub-modules may include any suitable computer-executable code or set of instructions (e.g., as would be executed by a suitably programmed processor, microprocessor, or CPU), such as computer-executable code corresponding to a programming language. For example, programming language source code may be compiled into computer-executable code. Alternatively, or in addition, the programming language may be an interpreted programming language such as a scripting language.

Each module may contain instructions which when executed by a programmed processor cause an apparatus (such as a server or client device) to perform the specific function or functions. The apparatus may be one or both of a client device or a remote server or platform. Therefore, a module may contain instructions that are performed (in whole or in part) by a client device, a server or platform, or both.

Each application module or sub-module may correspond to a specific function, method, process, or operation that is implemented by the module or sub-module. Each module or sub-module may contain a set of computer-executable instructions that when executed by a programmed processor or co-processors cause the processor or co-processors (or a device or devices in which they are contained) to perform the specific function, method, process, or operation. Such function, method, process, or operation may include those used to implement one or more aspects of the disclosed system and methods, such as for:

Identify the Types or Categories of Medical Data Associated with the Progression of a Disease or Illness (as suggested by module 406);

These represent types or sources of data (e.g., waveforms, images, lab results, other factors or indicators) that have been found useful in tracking the progression of a specific disease or illness;

in some sense, these are "markers" that may be monitored to determine if a disease or illness is progressing or resolving;

Acquire Examples of the Medical Data for a Set of Patients and Group the Medical Data of Each Type Into Data That Is Either Indicative or Not Indicative of a Specific Condition or Stage of the Disease or Illness (as suggested by module 408);

Train a Separate Machine Learning Model Using Each Type of Data and a Label of Whether that Data is Indicative or Not Indicative of the Specific Condition (as suggested by module 410);

Provide Medical Data of Each Type for a New Patient to the Trained Model(s) to Generate the Model Outputs for the New Patient (as suggested by module 411);

Note that although embodiments are described as assisting with the treatment of patients in a hospital setting, in some embodiments, data input to the model or models described herein may be obtain from a patient in a home-care environment with data provided by a tele-medicine system or other communication channel. This use case may be helpful in better managing use of hospital capacity, including emergency and ICU facilities;

Combine the Outputs of Each Model into a Composite Metric or Value Indicating the Likelihood (such as the probability) of the Patient Entering into the Specific Condition Based on the Input Data for that Patient (as suggested by module 411);

The composite metric may be formed from one or more of a weighted sum of the output of each model, a fit of the outputs to a polynomial or other function, a dynamically varying function of time that provides greater weighting based on the time since an event (such as entry to a hospital or ICU) and/or time since when specific data was collected);

Provide the Generated Composite Metric Indicating the Likelihood of the New Patient Entering into the Specific Condition to a Medical Professional for Evaluation (as suggested by module 414);

this may include generating an alert or notification on a user interface or generating a message to a medical services provider if the patient's condition has rapidly worsened or is expected to (e.g., because the value of the metric has changed more quickly than expected, because the value of the metric has reached a critical level, etc.); and Respond to the Evaluation of the Medical Professional by One or More of Initiating a Treatment Option, Acquiring Specific Equipment, etc. (this is optional and depends on the configuration of the system and its integration with user systems for generating alerts, requesting resources, etc.) (as suggested by module 415).

As mentioned, although for purposes of providing an example, an embodiment of the disclosed system and methods has been described in the context of providing medical care for a specific disease or illness (i.e., COVID-19 or one of its variants), the approach and techniques described may be applied to the treatment of other diseases, illnesses, or conditions. To assist in modifying or adapting the disclosed system and methods for use in the treatment of other diseases or illnesses, the following sections provide additional information regarding selection of the training data used, the trained models produced, the way the output(s) of the trained models are combined, and the interpretation of the combined outputs.

The described composite score, decision processes and models can be used for other diseases for which Acute Respiratory Distress Syndrome is a key factor that can lead to death as an outcome, and which may benefit from intervention. These include COPD, influenza, bacterial pneumonia, sepsis, lung and chest injury, and inhalation of harmful substances. As the model(s) become more refined through acquisition and use of additional training data, it is expected they may be used for other risk indicators aside from ARDS vs non-ARDS and in some cases, on a gradient scale.

With regards to changes that may be made to the models or decision processes when using the disclosed system and methods for treatment of other diseases or conditions:

The disclosed approach leverages raw data instead of inputs that push a physician or other clinical professional towards an assumed diagnosis. None of the inputs are entirely unique to COVID-19 in that they reflect lung function and inflammation at a basic level, although D-dimer is a lab marker that can be predictive of risk exclusively in COVID-19 patients;

If the system acquires training data for patients diagnosed with COPD, bacterial pneumonia, and influenza, it will then be able to adjust to match ARDS versus non-ARDS patients regardless of their actual disease state, as most of the inputs vary across different disease states;

To implement such a system, one may build sequestered training data sets for each disease state and instruct the model to examine each silo before generating an overall risk score;

With that as background, the reasons for selecting the described types or categories of training data (i.e., lung images, lab results, waveforms) used as part of the modeling and decision processes disclosed herein is described below, and these considerations may assist in selecting the appropriate type or source of data for treatment of other diseases or illnesses:

Waveforms: a reason for the choice of this type of data as training data and as inputs to a trained model is because of the way cardio-respiratory systems interact and are impacted by the disease (COVID in this example);

The waveforms (e.g., heart rate, blood pressure, SpO2, EKG) are impacted (in some cases in unique ways) by SARS-CoV-2 and by how the disease progresses in patients. For example, drops in SpO2 to as low as 88 percent saturation have correlated directly with severe disease progression. This is believed to be because of the way the virus attacks alveoli in the lungs, decreasing the surface area over which oxygen can transfer. As less oxygen is absorbed, heart rate (HR) and blood pressure (BP) increase to compensate. As BP and HR increase, the heart becomes more and more stressed. This increase in mechanical stress can cause anomalies in the rhythms of the heart which are reflected in the EKG measurements of the patient (the heart is overworked, and sinoatrial signals are disrupted; these signals are reflected in the EKG waveforms);

Lab results: as the disease progresses, alveoli die off rapidly, releasing signals for the body to send neutrophils into the area. The neutrophils then leverage signaling molecules such as interleukins and d-dimer to cause inflammation. Inflammation normally serves as a mechanism to restrict flow in or out of the area of infection such that the movement of the pathogen is restricted, and white blood cells can work to fight the disease. However, in viral infections such as SARS-CoV-2, this inflammation within the lungs simply accelerates the process by keeping a high viral load within the lungs and exacerbating and complicating the biomechanical impact that the cardio-respiratory module (i.e., the waveform detection and processing module) is intended to detect;

The lab information obtained usually correlates to the body beginning to fight off the disease and signals a progression of the body's response. However, if the body is unable to isolate the virus, it can initiate a phenomenon called a cytokine storm (such as monokine induced by interferon gamma, although other mechanisms are also possible) where the body causes general inflammation as response to the infection. At that point white blood cells start attacking several different types of cells. The consequences of this event are not fully understood; however, its initiation appears to correlate with increases in the three lab markers mentioned above (i.e., cytokines, interleukins, and D-dimers);

This increase exacerbates the mechanical problems, worsening the disease and increasing its harm to a patient. The cytokine storms are theorized to be a large part of the modality of death for H1N1 patients in the 1918 pandemic and appear to be how even young healthy people are succumbing to the COVID disease;

The cytokine storms are also a part of why the inventor(s) believe that ECMO (extracorporeal membrane oxygenation) treatment is so effective. The cytokines are communicated through blood plasma and ECMO involves removing the complete blood fluid, oxygenating it, and then returning it to the ascending vena cava. This approach skips some of the signaling pathways leveraged by the cytokines, effectively dampening the signal they are sending by rerouting it. The ECMO treatment effectively resets the level in the patient, making it more difficult for a cytokine storm to take place. In coordination with the cardio-respiratory module, this data/module can effectively track how close a patient is to entering ARDS when first admitted to the ICU;

Images: this type of data is specific for use with COVID-19 patients and other similarly affected patients. There is a unique imaging phenomenon that occurs in the lungs of COVID patients because of how aggressively it attacks the alveoli. The disease manifests as a crystalline lattice across the lungs, starting higher up and then progressing deeper as the disease worsens. This is due to how the virus travels and where viral loads are carried due to the fluid mechanics at the top of the lungs. This swirling effect in the lungs can allow the virus to exist in higher loads in the initial phase of the disease. The mass death of alveoli occurs further and further down the lung tissue as the disease worsens and the virus spreads from cell to cell;

This presents a progressive mechanism where the visible outputs appear to correlate with the severity of the disease state. By using this imaging data as an initial input to the system, it can allow an independent verification of the outputs of the other data sources/modules and strengthen the models;

There are distinct phenomena that appear in other disease states and the system can be trained to recognize these and automatically correlate these to a risk of developing ARDS (or another state). By segmenting these data inputs, the system can minimize the risk of cross talk between the data models (e.g., COPD progress to ARDS being mistaken for bacterial pneumonia progress to ARDS for example);

Dynamic Biasing of data inputs: because the cardio-respiratory (waveform) model is fed data from the patient monitoring systems, it can adjust to the input baselines dynamically and in real-time or pseudo real-time and therefore work from a larger data set, increasing the resolution of the outcome. Therefore, initially, this module's output may be accorded the highest weight across the three data inputs to the composite metric model.

As one example, within the waveform model, BP and SpO2 may initially be weighted the highest, then EKG, then HR due to the mechanical interplays described above and how they correlate to initial disease progression. However, the RCCM module will have the ability to dynamically change these relative weights due to their predictive power as presented by data being cycled back into the training data.

For instance, if EKG variance or HR irregularities begin to exhibit higher or lower positive predictive power, then the system will be able to adjust these weights dynamically as it examines other patients' data. And because the system may be architected to deliver services as a SaaS platform, patient weighting changes can benefit patients in completely different healthcare settings, systems, and even countries due to the use of shared data reservoirs. For example, if patients in Belgium provide training data that indicates lung imaging carries a positive predictive power higher than HR or BP, then the system may respond accordingly in the US, allowing improved predictions and treatments for patients in that country.

Below are further examples of what a physician or other clinical professional might do in terms of further treatment based on the generated composite risk metric:

One possible, although unfortunate example is use of the composite metric as part of decisions related to care rationing. If a patient is almost certain to go into ARDS and a care facility does not have an ECMO or ventilator available, but a supplemental oxygen supply or non-invasive ventilator can be redirected to a patient who is showing a lower risk of ARDS and who would have otherwise gone untreated, then the first patient may be denied care. This would change the outcome from one where both patients expire due to a misallocation of care, to one where at least one patient can survive due to the foresight provided by the system described herein;

A second example would be one in which an implicit bias can be counteracted. For example, if a patient is a young woman, she may be presumed to have a lower likelihood of entering a severe disease state due to the general societal assumptions regarding the disease and her age. However, if the system predicts that she is showing a higher correlation with biomechanical or chemical risk factors, then higher levels of care can be implemented in a way that are preventive instead of reactionary. In this example, the system functions to separate general understandings and distills them into raw data that is not influenced by such kinds of assumptions; and A third example would be one in which a facility has an ICU full of patients, all presenting with similar symptoms but not enough care equipment to go around. In this situation, the disclosed system can provide a physician or other clinical professional with information that allows them to predict the progression of the disease across different patients even if the patients' raw data appears similar. The physician can then prepare resources or triage the application of those resources according to their best judgement instead of having to react as various patients worsen at different rates.

Additionally, physicians and other clinical professionals can make decisions in reaction to the prediction in isolation. A patient whose mechanical symptoms appear to be a severe case, but their lab module outputs correlate to a less severe case may indicate that the patient is in an early progression state of the disease and therefore would respond extremely well to treatments that limit the reproduction and spread of the virus, such as monoclonal antibodies (or a treatment such as Remdesivir, an antiviral drug that prevents viral production in the cell). In this instance a combination of supplemental oxygen and these medications may yield better results than escalation to a ventilator.

In some embodiments, other calculations or models can be derived from or based on the training data and may be presented to and/or utilized by different processes of the overall system. Examples of these forms of data are given below:

The second derivative of an oxygenation curve may provide higher positive predictive power than other variables, as a graph of SpO2 versus time could include a second order derivative that indicates an inflection point in the curvature. Patients who are entering more severe stages of COVID-19 usually show a sharp decline in oxygenation levels. By monitoring predictive derivatives, one can monitor when these declines may be beginning in a more subtle manner;

Additionally, second derivative curves for blood pressure and QT segment elongation incidence versus time may be used in a similarly predictive manner. As these values go from positive to negative on the y-axis when charted versus time, a likelihood of sharp changes arises. The QT Segment variance may need to be analyzed in the opposite manner by charting when it crosses from negative to positive as these elongation frequencies tend to increase with cardiac distress, an early indicator of ARDS;

1. These three training features can be combined to make up a whole or part of the cardio-respiratory (waveform) risk module output. In one example, each feature can be scaled by the central node of the cardio-respiratory module by both a scalar and exponential value:

$$\text{Risk ARDS}(t) = 4(SpO2(t)'')^5 + 3(BP(t)'')^3 | + 2(QT/s/s(t)'')|^2$$

where 4 is the scalar for SpO2 versus time and 5 is the exponential, etc.

In some embodiments, the Labs and Image model outputs may be used in determining the overall (composite) risk metric when they become available and stabilized but may be discounted until a certain period has passed (such as 24 hours for labs and 6 hours for an x-ray). Note that their contribution to the overall risk score may not change significantly over time unless new labs are run sufficiently frequently. In the case where such values are unavailable, the risk score may be appropriately weighted to consider them multiplied by zero; this will result in the overall risk not being biased when the data is not available.

In some embodiments, a dedicated node of one or more of the models may operate under a crisis monitoring assumption if a lab output or x-ray output is not available during a care rationing scenario. In such a situation, the node may add a risk scalar standardized for care rationing situations. This may help ensure that risk is not disproportionately downscaled due to the lack of lab or x-ray outputs.

The composite risk metric can be used to correlate recommendations to physicians and other clinical professionals by providing context data when the metric exceeds a threshold value, or a metric is within a certain range (where the threshold or range may be set by doctor as a "rule" to trigger a recommendation). For instance, if the SpO2 based data shows a sharp curvature, physicians or other clinical professionals can formulate treatment regimens that preemptively suggest supplemental oxygen. As the risk value increases, more intensive interventions may be suggested. These may include non-invasive and then invasive ventilation, then ECMO, for example;

The thresholds or ranges may be set by a medical professional based on their experience and judgment and may be set or refined by use of a trained machine learning model that "learns" what resources, treatments, or recommendations are made by a medical professional (or group of them) when certain risk metric values are present, or when the situations that cause a model to generate those values are present (such as a specific set or type of lab data, image, etc.).

One additional value of the disclosed system is the ability to consider non-obvious therapies, such as nasal high flow ventilation and ECMO treatments based on risk scaling. This provides extra value due to the broad basis of the training data and unique methods by which the nodes examine the various inputs;

For example, nasal high flow may be used as a stepping-stone between supplemental oxygenation and invasive ventilation; this may be a preferable approach because roughly 80 percent of invasive ventilation patients do not survive that treatment when they are suffering from COVID-19. It is theorized that this is due to inflammatory reactions to invasive ventilation contributing to the overall decline in condition of these patients; therefore, if the labs module output spikes, invasive ventilation may not be the best course of action, at least initially;

Additionally, if the cardio elements of the cardio-respiratory (waveform) module increase in severity while the other variables are stabilized, ECMO or other cardiovascular treatments may be the best treatment.

One way in which patient data could be presented is by creating a "normal" risk curve from the training data and showing a healthcare worker where a given patient lies on that curve instead of presenting a single risk metric. This may enable a physician or other clinical professional to observe their patients' risks relative to the overall number of COVID-19 patients and better enable them to recommend effective therapies.

Another way that healthcare workers can interact with the data is by viewing a top-level dashboard that shows the current risk score of the patient output by the trained models and allows them to generate reports that show trends for specific combinations of data. These may include the combined curves of the cardio-respiratory calculations, or the weight given to an x-ray image by the system.

In addition to the clinical value of the disclosed system, public health benefits could be realized by scaling the visibility of the trending risk score data across larger and larger groups, while de-identifying (anonymizing) data to comply with various regulatory and privacy standards. As non-limiting examples:

Allow hospitals to see resource needs across departments and enable them to better plan device, human resource, and oxygen capacity within the hospital;

This could mean scheduling a larger grouping of respiratory therapists to the ER due to a large influx of patients who are there due to current bed capacity in the ICU or COVID ward;

This may also include purchase planning for higher volumes of liquid oxygen, or the activation of a secondary oxygen generator located in the hospital;

This may even contribute to better capital planning for construction resources in the instances where a large influx of ER COVID patients contributes to a capacity problem and rooms with negative pressure and high-volume oxygen lines must be built with very little notice. The system may provide benefits if trending data is considered during short term planning sessions;

Allow hospital systems to see need across various facilities;

This would entail the same benefits of the above example but for multiple facilities;

This may also allow movement of equipment from one facility to another to boost short term capacity in between purchasing cycles;

This may influence a decision to let staff work across facilities and effectively isolate shifts to limit spread amongst them by limiting the movement of staff from one facility to another.

Allow governments to see need across regions;

If a governmental entity sees an uptick in severe symptoms or predicted symptoms in one region, they may choose to implement non pharmaceutical interventions such as mask wearing or closure of schools with early warning and in a targeted manner as opposed to region-wide interventions. This could pay major economic dividends;

Additionally, a regional government may choose to reallocate a central repository of medical resources such as capital equipment, masks, or ventilators in such a way to combat indicators of severe symptoms. Severe symptoms, such as those predicted by the disclosed models, have been shown to correlate with higher viral load and therefore are more infectious. Therefore, more severe patients could act as a public health predictor of an uptick in cases;

Allow public health officials to track deviations and find novel conditions;

Governments may also choose to monitor the model outputs in such a way that one can detect variants in COVID-19 or even novel conditions that have similar symptomatology but are a novel disease;

For instance, if one were to have available the SpO2 versus time curvature for a set of patients, it is theoretically possible to have spotted variances that could have led to the identification of SARS-CoV-2 earlier. A system such as this invention implemented at a regional level that carries de-identified data in real time to public health officials, could therefore act as an early warning system;

Additionally, even in COVID-19 patients, variants, such as the B.1.1.7 first identified in the UK, cause different sets of symptoms. For example, patients with the variant in New Zealand report a more flu-like symptomology with aches and muscle pain versus previous COVID-19 cases who present more respiratory symptoms. This could enable governments to spot deviations in underlying health indicators such as the ones monitored by the disclosed system and track variants at a population level rather than depending purely on wastewater monitoring or a surveillance PCR testing program which can be expensive and burdensome to maintain;

These public health benefits can be expanded to zoonotic disease monitoring. Of the zoonotic diseases that have emerged in the 21st century, the majority have been respiratory diseases that cause complications in cardiovascular function and widespread inflammation (e.g., SARS, MERS, H1N1, H5N8, COVID-19). By tuning the disclosed models to identify large deviations across regional populations in the risk factors or "features" of the input data, the disclosed system may be used to identify possible variants. This could be similar to the wastewater monitoring systems currently being used to track variants in Italy and the United States.

Figure 5:
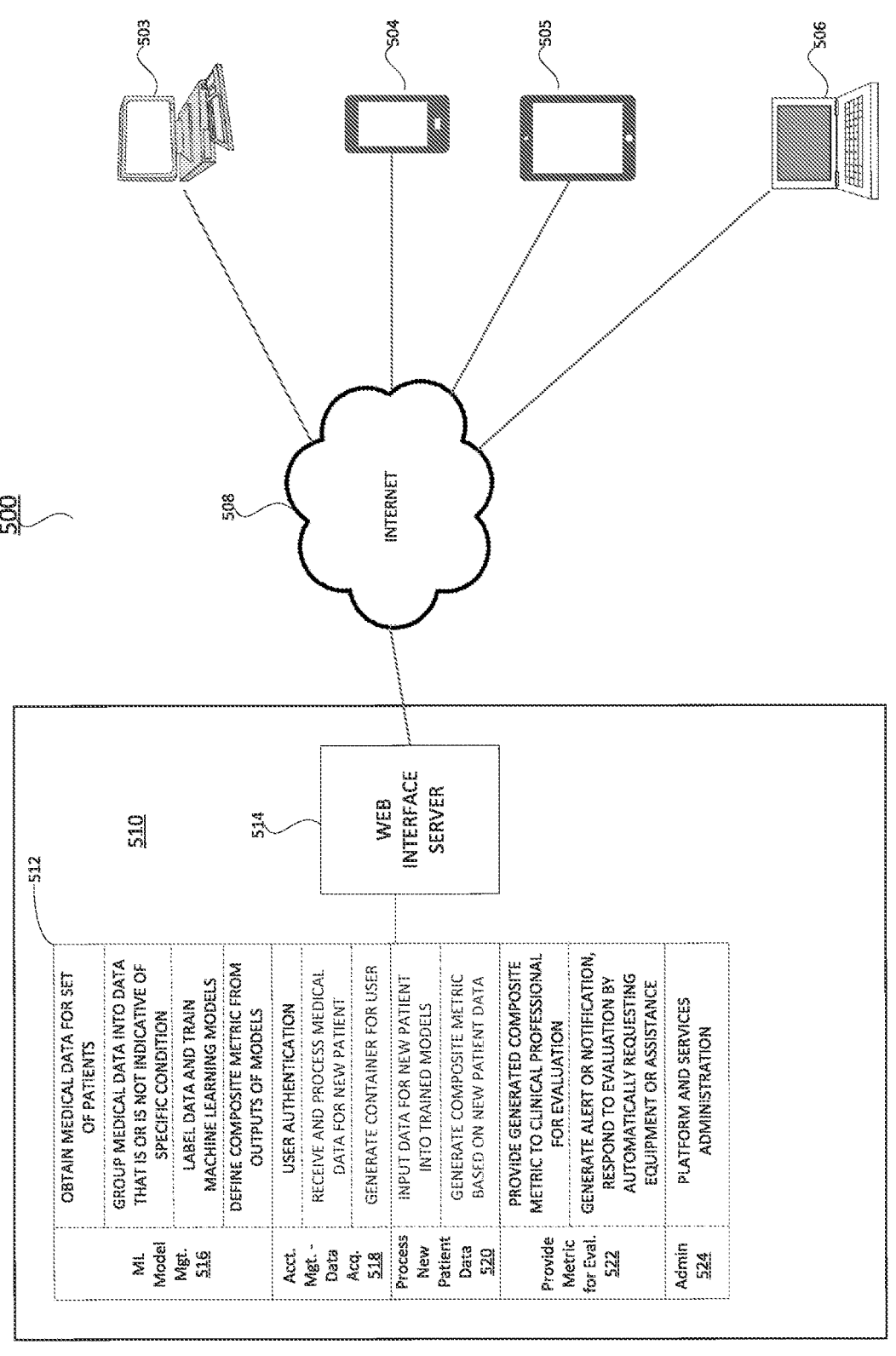
FIGS. 5-7 are diagrams illustrating an architecture for a multi-tenant or SaaS platform that may be used in implementing an embodiment of the systems and methods described herein.
Figure 6:
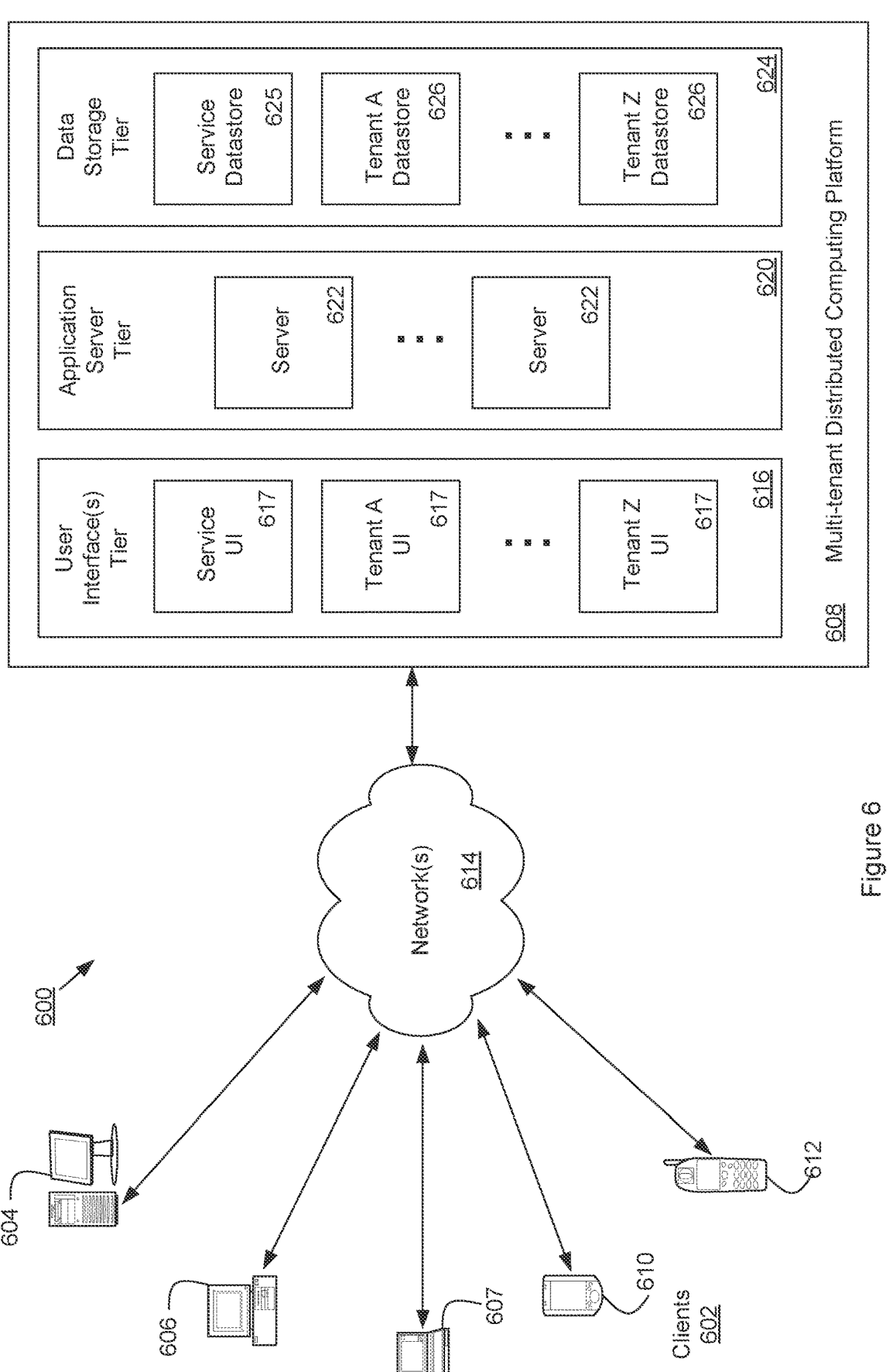
Figure 7:
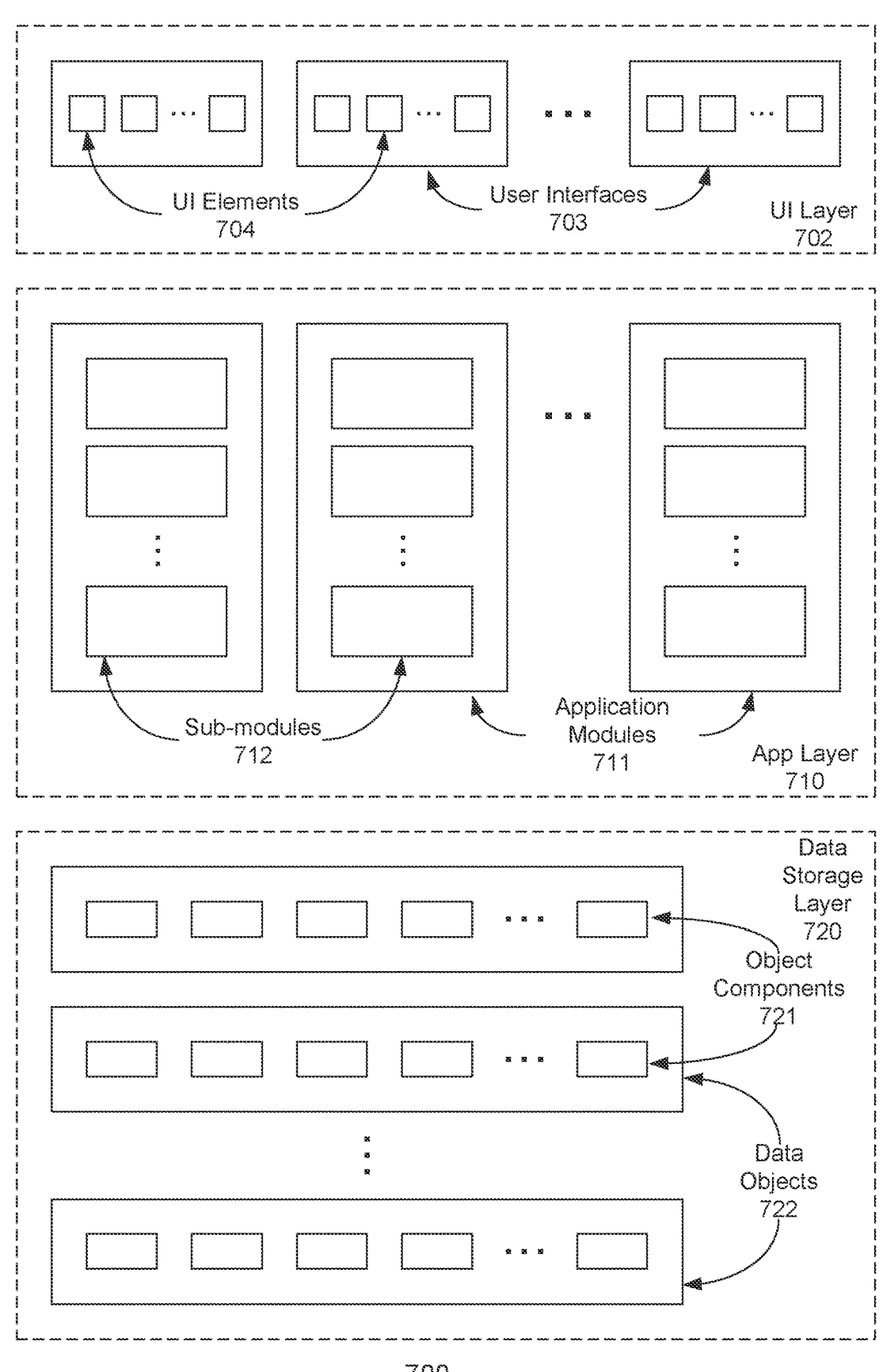

In some embodiments, the functionality and services provided by the system and methods described herein may be made available to multiple users by accessing an account maintained by a server or service platform. Such a server or service platform may be termed a form of Software-as-a-Service (SaaS). FIG. 5 is a diagram illustrating a SaaS system in which an embodiment of the invention may be implemented. FIG. 6 is a diagram illustrating elements or components of an example operating environment in which an embodiment of the invention may be implemented. FIG. 7 is a diagram illustrating additional details of the elements or components of the multi-tenant distributed computing service platform of FIG. 6, in which an embodiment of the invention may be implemented.

In some embodiments, the system or services described herein for Analyzing Patient Data and Allocating Medical Equipment and Other Resources may be implemented as micro-services, processes, workflows, or functions performed in response to the submission of patient medical data. The micro-services, processes, workflows, or functions may be performed by a server, data processing element, platform, or system. In some embodiments, the data analysis and other services may be provided by a service platform located "in the cloud". In such embodiments, the platform may be accessible through APIs and SDKs. The functions, processes and capabilities described herein and with reference to the Figures may be provided as micro-services within the platform. The interfaces to the micro-services may be defined by REST and GraphQL endpoints. An administrative console may allow users or an administrator to securely access the underlying request and response data, manage accounts and access, and in some cases, modify the processing workflow or configuration.

Note that although FIGS. 5-7 illustrate a multi-tenant or SaaS architecture that may be used for the delivery of business-related or other applications and services to multiple accounts/users, such an architecture may also be used to deliver other types of data processing services and provide access to other applications. For example, such an architecture may be used to provide the medical data analysis and resource allocation services described herein. Although in some embodiments, a platform or system of the type illustrated in FIGS. 5-7 may be operated by a $3^{rd}$ party provider to provide a specific set of business-related applications, in other embodiments, the platform may be operated by a provider and a different business may provide the applications or services for users through the platform.

FIG. 5 is a diagram illustrating a system 500 in which an embodiment of the invention may be implemented or through which an embodiment of the services described herein may be accessed. In accordance with the advantages of an application service provider (ASP) hosted business service system (such as a multi-tenant data processing platform), users of the services described herein may comprise individuals, businesses, stores, organizations, etc. A user may access the application testing and evaluation services using any suitable client, including but not limited to desktop computers, laptop computers, tablet computers, scanners, smartphones, etc. In general, any client device having access to the Internet may be used to provide patient data to the platform for processing and evaluation. A user interfaces with the service platform across the Internet 508 or another suitable communications network or combination of networks. Examples of suitable client devices include desktop computers 503, smartphones 504, tablet computers 505, or laptop computers 506.

Medical Data Analysis and Resource Allocation system 510, which may be hosted by a validated third party using controlled server architecture, may include a set of data analysis and other services to assist in the allocation of medical resources, such as equipment, treatments, and expertise 512, and a web interface server 514, coupled as shown in FIG. 5. It is to be appreciated that either or both data analysis and other services 512 and the web interface server 514 may be implemented on one or more different hardware systems and components, even though represented as singular units in FIG. 5. Data Analysis and Resource Allocation services 512 may include one or more functions or operations for the evaluation of patient medical data to generate a metric representing the likelihood or probability of the patient entering a specific medical condition or stage of the progression of their disease or illness.

In some embodiments, the set of services available to a user (such as a hospital, group of medical professionals, insurance company, independent consultant, etc.) may include one or more that perform the functions and methods described herein for analysis and evaluation of medical data and generation of a metric characterizing the likelihood of a patient entering a specific condition or stage of progression of their disease or illness. In some embodiments and depending upon the configuration of the system and integration with a user's systems, the metric may be used to generate an alert, a notification, or a request for a specific resource (such as an ECMO machine or ventilator) to be made available for the patient.

As examples, in some embodiments, the set of application testing, evaluation, and reporting functions, operations or services made available through the platform or system 510 may include:

Machine Learning Model Management services 516, such as
   a process or service to obtain a set of medical data of one or more types (such as images, lab results, waveforms, etc.) for a set of patients;
   a process or service to group each type of data into data that is either indicative or not indicative of (i.e., associated with or not associated with) a specific condition or stage of a disease or illness;
   a processor service to label or annotate the set of data of each type and group to indicate whether it is indicative or not indicative of the specific condition or stage of the disease or illness;
   a process or service to train a machine learning model for each type of data;
      each model generates as an output a probability, confidence level, metric or other value representing the likelihood that a patient having medical data of that type will enter into that specific condition or stage of their disease or illness;
   a process or service to define a composite metric or value by combining the outputs of the trained models, where the composite metric or value represents an overall likelihood of a patient entering that specific condition or stage of their disease or illness;
Account Management and Data Acquisition services 518, such as
   a process or service to authenticate a user (such as a physician, hospital, insurance company, group of practitioners, etc.) wishing to submit a set of patient data for analysis and evaluation;
   a process or service to receive and process medical data of one or more types or categories for a new patient;
      in some embodiments, this may include processes to assign an identifier to the patient data and to store an anonymized version of the data for later use as training data for a model;
   a process or service to generate a container or instantiation of the medical data analysis and evaluation services for the new patient's data;
Process New Patient Data services 520, such as
   a process or service to input the medical data of each type for the new patient into the appropriate machine learning model;
   a process or service to generate the composite metric or value representing an overall likelihood of the patient entering the specific condition or stage of their disease or illness based on the outputs of each ML model;

Provide Composite Metric for Evaluation processes or service 522, such as a process or service to provide the generated composite metric for the new patient to a medical professional for evaluation;

depending on the configuration of the system and/or integration with the user's systems, the metric may be displayed on a piece of equipment or monitor, provided to the medical professional's private device, messaged, or texted to the medical professional, etc.;

a process or service to generate an alert or notification based on the value or change in value of the metric overtime;

depending on the configuration of the system and/or integration with the user's systems, the alert or notification may be displayed on a piece of equipment or monitor, provided to the medical professional's private device, messaged, or texted to the medical professional, etc.;

based on one or more of the metrics, the alert or notification, or the evaluation by the medical professional, automatically requesting that certain equipment, treatments, or expertise be made available for the patient;

Administrative services 524, such as a process or services to enable the provider of the medical data analysis and evaluation services and/or the platform to administer and configure the processes and services provided to users, such as by altering how the composite metric is calculated for all or for certain patients, altering the weighting of the outputs of the individual trained models, altering the types or labelling of data used to train a model, altering the conditions that result in generating an alert or notification, etc.

The platform or system shown in FIG. 5 may be hosted on a distributed computing system made up of at least one, but likely multiple, "servers." A server is a physical computer dedicated to providing data storage and an execution environment for one or more software applications or services intended to serve the needs of the users of other computers that are in data communication with the server, for instance via a public network such as the Internet. The server, and the services it provides, may be referred to as the "host" and the remote computers, and the software applications running on the remote computers being served may be referred to as "clients." Depending on the computing service(s) that a server offers it could be referred to as a database server, data storage server, file server, mail server, print server, web server, etc. A web server is commonly a combination of hardware and the software that helps deliver content, commonly by hosting a website, to client web browsers that access the web server via the Internet.

FIG. 6 is a diagram illustrating elements or components of an example operating environment 600 in which an embodiment of the invention may be implemented. As shown, a variety of clients 602 incorporating and/or incorporated into a variety of computing devices may communicate with a multi-tenant service platform 608 through one or more networks 614. For example, a client may incorporate and/or be incorporated into a client application (e.g., software) implemented at least in part by one or more of the computing devices. Examples of suitable computing devices include personal computers, server computers 604, desktop computers 606, laptop computers 607, notebook computers, tablet computers or personal digital assistants (PDAs) 610, smart phones 612, cell phones, and consumer electronic devices incorporating one or more computing device components, such as one or more electronic processors, microprocessors, central processing units (CPU), or controllers. Examples of suitable networks 614 include networks utilizing wired and/or wireless communication technologies and networks operating in accordance with any suitable networking and/or communication protocol (e.g., the Internet).

The distributed computing service/platform (which may also be referred to as a multi-tenant data processing platform) 608 may include multiple processing tiers, including a user interface tier 616, an application server tier 620, and a data storage tier 624. The user interface tier 616 may maintain multiple user interfaces 617, including graphical user interfaces and/or web-based interfaces. The user interfaces may include a default user interface for the service to provide access to applications and data for a user or "tenant" of the service (depicted as "Service UI" in the figure), as well as one or more user interfaces that have been specialized/customized in accordance with user specific requirements (e.g., represented by "Tenant A UI", . . . , "Tenant Z UI" in the figure, and which may be accessed via one or more APIs).

The default user interface may include user interface components enabling a tenant to administer the tenant's access to and use of the functions and capabilities provided by the service platform. This may include accessing tenant data, launching an instantiation of a specific application, causing the execution of specific data processing operations, etc. Each application server or processing tier 622 shown in the figure may be implemented with a set of computers and/or components including computer servers and processors, and may perform various functions, methods, processes, or operations as determined by the execution of a software application or set of instructions. The data storage tier 624 may include one or more data stores, which may include a Service Data store 625 and one or more Tenant Data stores 626. Data stores may be implemented with any suitable data storage technology, including structured query language (SQL) based relational database management systems (RDBMS).

Service Platform 608 may be multi-tenant and may be operated by an entity in order to provide multiple tenants with a set of business-related or other data processing applications, data storage, and functionality. For example, the applications and functionality may include providing web-based access to the functionality used by a business to provide services to end-users, thereby allowing a user with a browser and an Internet or intranet connection to view, enter, process, or modify certain types of information. Such functions or applications are typically implemented by one or more modules of software code/instructions that are maintained on and executed by one or more servers 622 that are part of the platform's Application Server Tier 620. As noted with regards to FIG. 5, the platform system shown in FIG. 6 may be hosted on a distributed computing system made up of at least one, but typically multiple, "servers."

As mentioned, rather than build and maintain such a platform or system themselves, a business may utilize systems provided by a third party. A third party may implement a business system/platform as described above in the context of a multi-tenant platform, where individual instantiations of a business' data processing workflow (such as the medical data analysis and evaluation services and processing described herein) are provided to users, with each business representing a tenant of the platform. One advantage to such multi-tenant platforms is the ability for each tenant to customize their instantiation of the data processing workflow to that tenant's specific business needs or operational methods. Each tenant may be a business or entity that uses the multi-tenant platform to provide business services and functionality to multiple users.

FIG. 7 is a diagram illustrating additional details of the elements or components of the multi-tenant distributed computing service platform of FIG. 6, in which an embodiment of the invention may be implemented. The software architecture shown in FIG. 7 represents an example of an architecture which may be used to implement an embodiment of the invention. In general, an embodiment of the invention may be implemented using a set of software instructions that are designed to be executed by a suitably programmed processing element (such as a CPU, microprocessor, processor, controller, computing device, etc.). In a complex system such instructions are typically arranged into "modules" with each such module performing a specific task, process, function, or operation. The entire set of modules may be controlled or coordinated in their operation by an operating system (OS) or other form of organizational platform.

As noted, FIG. 7 is a diagram illustrating additional details of the elements or components 700 of a multi-tenant distributed computing service platform, in which an embodiment of the invention may be implemented. The example architecture includes a user interface layer or tier 702 having one or more user interfaces 703. Examples of such user interfaces include graphical user interfaces and application programming interfaces (APIs). Each user interface may include one or more interface elements 704. For example, users may interact with interface elements to access functionality and/or data provided by application and/or data storage layers of the example architecture. Examples of graphical user interface elements include buttons, menus, checkboxes, drop-down lists, scrollbars, sliders, spinners, text boxes, icons, labels, progress bars, status bars, toolbars, windows, hyperlinks, and dialog boxes. Application programming interfaces may be local or remote and may include interface elements such as parameterized procedure calls, programmatic objects, and messaging protocols.

The application layer 710 may include one or more application modules 711, each having one or more submodules 712. Each application module 711 or sub-module 712 may correspond to a function, method, process, or operation that is implemented by the module or sub-module (e.g., a function or process related to providing business related data processing and services to a user of the platform). Such function, method, process, or operation may include those used to implement one or more aspects of the inventive system and methods, such as for one or more of the processes or functions described with reference to the Figures:

Identify the Types or Categories of Medical Data Associated with the Progression of a Disease or Illness;

Acquire Examples of the Medical Data for a Set of Patients and Group the Medical Data of Each Type Into Data That Is Either Indicative or Not Indicative of a Specific Condition or Stage of the Disease or Illness;

Train a Separate Machine Learning Model Using Each Type of Data and a Label of Whether that Data is Indicative or Not Indicative of the Specific Condition;

Define an overall or composite metric based on the outputs of the trained models;

Provide Medical Data of Each Type for a New Patient to the Trained Model(s) to Generate the Metric for the New Patient;

Combine the Outputs of Each Model into a Composite Metric or Value Indicating the Likelihood (such as the probability) of the Patient Entering into the Specific Condition Based on the Input Data for that Patient;

Provide the Generated Composite Metric Indicating the Likelihood of the New Patient Entering into the Specific Condition to a Medical Professional for Evaluation;

where the metric may be provided by a display, message, or other form presentation; and Respond to the Evaluation of the Medical Professional by One or More of Initiating a Treatment Option, Acquiring Specific Equipment, etc. (this is optional and depends on the configuration of the system and its integration with user systems for generating alerts, requesting resources, etc.);

In some embodiments, this may be an automated or semi-automated process wherein based on a range or threshold value for the composite metric (or for one or more of the individual metrics), a decision is made whether to initiate a specific process or resource request. The range or threshold value may be set by a medical professional and/or set based on the output of a trained model that "learns" the desired behavior of that professional or a group of professionals from a set of data representing previously treated patients.

The application modules and/or sub-modules may include any suitable computer-executable code or set of instructions (e.g., as would be executed by a suitably programmed processor, microprocessor, or CPU), such as computer-executable code corresponding to a programming language. For example, programming language source code may be compiled into computer-executable code. Alternatively, or in addition, the programming language may be an interpreted programming language such as a scripting language. Each application server (e.g., as represented by element 622 of FIG. 6) may include each application module. Alternatively, different application servers may include different sets of application modules. Such sets may be disjoint or overlapping.

The data storage layer 720 may include one or more data objects 722 each having one or more data object components 721, such as attributes and/or behaviors. For example, the data objects may correspond to tables of a relational database, and the data object components may correspond to columns or fields of such tables. Alternatively, or in addition, the data objects may correspond to data records having fields and associated services. Alternatively, or in addition, the data objects may correspond to persistent instances of programmatic data objects, such as structures and classes. Each data store in the data storage layer may include each data object. Alternatively, different data stores may include different sets of data objects. Such sets may be disjoint or overlapping.

Note that the example computing environments depicted in FIGS. 5-7 are not intended to be limiting examples. Further environments in which an embodiment of the invention may be implemented in whole or in part include devices (including mobile devices), software applications, systems, apparatuses, networks, SaaS platforms, IaaS (infrastructure-as-a-service) platforms, or other configurable components that may be used by multiple users for data entry, data processing, application execution, or data review.

The disclosure includes the following clauses and embodiments:

Clause 1. A method of assessing the status of a patient, comprising:

determining a current state of a medical condition of the patient;

determining a likelihood of the patient entering a more severe state of the medical condition than the current state, wherein determining the likelihood of the patient entering a more severe state of the medical condition further comprises;

acquiring data characterizing the current state of the medical condition of the patient, the acquired data including at least two different types or sources of data;

for each different type or source of data, inputting the data characterizing the current state of the medical condition of the patient into one of a plurality of models trained to output a metric representing a likelihood of the patient entering the more severe state of the medical condition based on the input data;

combining the output of each of the plurality of models into a composite metric, the composite metric representing the likelihood of the patient condition entering the more severe state of the medical condition; and generating an output comprising the composite metric for evaluation by a clinical professional, the composite metric used by the clinical professional to determine a treatment approach for the patient.

Clause 2. The method of clause 1, wherein the acquired data comprises two or more of lab results, x-rays, ultrasound images, lung images, waveforms indicating a state of the patient's organs or body functions, clinical observations, and psychological profile information.

Clause 3. The method of clause 1, wherein the medical condition is a viral infection, and further, wherein the viral infection is a coronavirus.

Clause 4. The method of clause 1, wherein the treatment approach includes allocating a resource to treat the patient, and the resource is an item of medical equipment, a staff member, a trained operator, a doctor, a nurse, a hospital bed, or another aspect of a hospital's capacity to treat patients.

Clause 5. The method of clause 1, wherein combining the output of each model into a composite metric further comprises generating a weighted combination of the metrics output by each of the trained models, and further, wherein the weights are a function of the amount of time since the current state of the medical condition of the patient was determined.

Clause 6. The method of clause 1, wherein generating an output comprising the composite metric for evaluation by a clinical professional further comprises generating a display of the composite metric on a device viewable by the clinical professional.

Clause 7. The method of clause 1, further comprising:

accessing information describing a level of a resource expected to be needed to treat the patient if the medical condition of the patient enters the more severe state; and generating a display of the composite metric and the accessed information describing the level of the resource expected to be needed on a device viewable by the clinical professional.

Clause 8. The method of clause 7, further comprising receiving an instruction from the clinical professional to alter the current level of the resource to the level of the resource expected to be needed to treat the patient if the medical condition of the patient enters the more severe state.

Clause 9. The method of clause 1, wherein each model is trained by a process comprising:

identifying a type of medical data associated with progression of a disease or illness;

acquiring examples of the identified type of medical data for a set of patients;

separating the acquired examples of the medical data into a first group indicative of a specific stage of the disease or illness and a second group that is not indicative of the specific stage of the disease or illness; and training the model using each group of data and an associated label, wherein the associated label indicates whether the group of data is indicative or is not indicative of the specific stage of the disease or illness.

Clause 10. The method of clause 1, wherein the more severe state of the medical condition indicated by the combined metric is Acute Respiratory Distress Syndrome (ARDS).

Clause 11. A system for assessing the status of a patient, comprising:

one or more electronic processors configured to execute a set of computer-executable instructions;

one or more non-transitory electronic data storage media containing the set of computer-executable instructions, wherein when executed, the instructions cause the one or more electronic processors to determine a current state of a medical condition of the patient;

determine a likelihood of the patient entering a more severe state of the medical condition than the current state, wherein determining the likelihood of the patient entering a more severe state of the medical condition further comprises;

acquire data characterizing the current state of the medical condition of the patient, the acquired data including at least two different types or sources of data;

for each different type or source of data, input the data characterizing the current state of the medical condition of the patient into one of a plurality of models trained to output a metric representing a likelihood of the patient entering the more severe state of the medical condition based on the input data;

combine the output of each of the plurality of models into a composite metric, the composite metric representing the likelihood of the patient condition entering the more severe state of the medical condition; and generate an output comprising the composite metric for evaluation by a clinical professional, the composite metric used by the clinical professional to determine a treatment approach for the patient.

Clause 12. The system of clause 11, wherein the acquired data comprises two or more of lab results, X-rays, ultrasound images, waveforms or signals indicating a state of the patient's organs or body functions, clinical observations, and psychological profile information.

Clause 13. The system of clause 11, wherein the medical condition is a viral infection, and further, wherein the viral infection is a coronavirus.

Clause 14. The system of clause 11, wherein the treatment approach includes allocating a resource to treat the patient, and the resource is an item of medical equipment, a staff member, a trained operator, a doctor, a nurse, a hospital bed, or another aspect of a hospital's capacity to treat patients.

Clause 15. The system of clause 11, wherein combining the output of each model into a composite metric further comprises generating a weighted combination of the metrics output by each of the trained models, and further, wherein the weights are a function of the amount of time since the current state of the medical condition of the patient was determined.

Clause 16. The system of clause 11, wherein generating an output comprising the composite metric for evaluation by a clinical professional further comprises generating a display of the composite metric on a device viewable by the clinical professional.

Clause 17. The system of clause 11, wherein the instructions further cause the one or more electronic processors to access information describing a level of a resource expected to be needed to treat the patient if the medical condition of the patient enters the more severe state; and generate a display of the composite metric and the accessed information describing the level of the resource expected to be needed on a device viewable by the clinical professional.

Clause 18. The system of clause 17, wherein the instructions further cause the one or more electronic processors to receive an instruction from the clinical professional to alter the current level of the resource to the level of the resource expected to be needed to treat the patient if the medical condition of the patient enters the more severe state.

Clause 19. One or more non-transitory computer-readable media comprising a set of computer-executable instructions that when executed by one or more programmed electronic processors, cause the processors to assess the status of a patient by:

determining a current state of a medical condition of the patient;

determining a likelihood of the patient entering a more severe state of the medical condition than the current state, wherein determining the likelihood of the patient entering a more severe state of the medical condition further comprises;

acquiring data characterizing the current state of the medical condition of the patient, the acquired data including at least two different types or sources of data;

for each different type or source of data, inputting the data characterizing the current state of the medical condition of the patient into one of a plurality of models trained to output a metric representing a likelihood of the patient entering the more severe state of the medical condition based on the input data;

combining the output of each of the plurality of models into a composite metric, the composite metric representing the likelihood of the patient condition entering the more severe state of the medical condition; and generating an output comprising the composite metric for evaluation by a clinical professional, the composite metric used by the clinical professional to determine a treatment approach for the patient.

Clause 20. The one or more non-transitory computer-readable media of clause 19, wherein the acquired data comprises two or more of lab results, X-rays, ultrasound images, waveforms or signals indicating a state of the patient's organs or body functions, clinical observations, and psychological profile information, and wherein the treatment approach includes allocating a resource to treat the patient, where the resource is an item of medical equipment, a staff member, a trained operator, a doctor, a nurse, a hospital bed, or another aspect of a hospital's capacity to treat patients.

Clause 21. The one or more non-transitory computer-readable media of clause 19, wherein combining the output of each model into a composite metric further comprises generating a weighted combination of the metrics output by each of the trained models, and further, wherein the weights are a function of the amount of time since the current state of the medical condition of the patient was determined.

Clause 22. The method of clause 1, wherein the medical condition is an illness or disease.

Clause 23. The method of clause 3, wherein the coronavirus is COVID-19.

Clause 24. The method of clause 4, wherein the resource is an extracorporeal membrane oxygenation (ECMO) machine.

Clause 25. The method of clause 1, wherein three trained models are used, and wherein an input to a first model is lab results, an input to a second model is Cardio-Respiratory data, and an input to a third model is lung image data.

Clause 26. The method of clause 1, wherein the more severe state of the medical condition indicated by the combined metric is Acute Respiratory Distress Syndrome (ARDS).

Clause 27. The method of clause 1, wherein the composite metric is used to automatically generate a recommendation or suggestion regarding allocation of a resource to treat the patient.

Clause 28. The method of clause 27, wherein the method further comprises using a rule-set or trained model to generate the recommendation or suggestion.

Clause 29. The method of clause 1 wherein acquiring data characterizing the current state of the medical condition of the patient further comprises acquiring the data from a patient data management system in a hospital where the patient is located.

Clause 30. A system for assessing a status of a patient, comprising:

an element to acquire data representing a current state of a medical condition of the patient from a patient data management system of a hospital, wherein the acquired data is at least two different types of data;

a plurality of trained models, with one trained model configured to receive each type of data as an input, and in response to generate an output representing a measure of the likelihood that the patient will enter a more severe state of the medical condition; and an executed process to combine the outputs of each of the plurality of trained models into a composite metric for evaluation by a clinical professional, the composite metric used by the clinical professional to determine a treatment approach for the patient.

Clause 31. The system of clause 30, wherein the acquired data comprises two or more of lab results, x-rays, ultrasound images, lung images, waveforms indicating a state of the patient's organs or body functions, clinical observations, and psychological profile information.

Clause 32. The system of clause 30, wherein the medical condition is a viral infection, and further, wherein the viral infection is a coronavirus.

Clause 33. The system of clause 30, herein the treatment approach includes allocating a resource to treat the patient, and the resource is an item of medical equipment, a staff member, a trained operator, a doctor, a nurse, a hospital bed, or another aspect of a hospital's capacity to treat patients.

Clause 34. The system of clause 30, wherein combining the output of each model into a composite metric further comprises generating a weighted combination of the metrics output by each of the trained models, and further, wherein the weights are a function of the amount of time since the current state of the medical condition of the patient was determined.

The present invention as described above can be implemented in the form of control logic using computer software in a modular or integrated manner. Based on the disclosure and teachings provided herein, a person of ordinary skill in the art will know and appreciate other ways and/or methods to implement the present invention using hardware and a combination of hardware and software.

In some embodiments, certain of the methods, models or functions described herein may be embodied in the form of a trained neural network or machine learning model, where the network or model is implemented by the execution of a set of computer-executable instructions. The instructions may be stored in (or on) a non-transitory computer-readable medium and executed by a programmed processor or processing element. The specific form of the method, model or function may be used to define one or more of the operations, functions, processes, or methods used in the development or operation of a neural network, the application of a machine learning technique or techniques, or the development or implementation of an appropriate decision process. Note that a neural network or deep learning model may be characterized in the form of a data structure in which are stored data representing a set of layers containing nodes, and connections between nodes in different layers are created (or formed) that operate on an input to provide a decision or value as an output.

In general terms, a neural network may be viewed as a system of interconnected artificial "neurons" or nodes that exchange messages between each other. The connections have numeric weights that are "tuned" during a training process, so that a properly trained network will respond correctly when presented with an image or pattern to recognize (for example). In this characterization, the network consists of multiple layers of feature-detecting "neurons"; each layer has neurons that respond to different combinations of inputs from the previous layers. Training of a network is performed using a "labeled" dataset of inputs in a wide assortment of representative input patterns that are associated with their intended output response. Training uses general-purpose methods to iteratively determine the weights for intermediate and final feature neurons. In terms of a computational model, each neuron calculates the dot product of inputs and weights, adds the bias, and applies a non-linear trigger or activation function (for example, using a sigmoid response function).

A machine learning model is a set of layers of connected neurons that operate to make a decision (such as a classification) regarding a sample of input data. A model is typically trained by inputting multiple examples of input data and an associated correct "response" or decision regarding each set of input data. Thus, each input data example is associated with a label or other indicator of the correct response that a properly trained model should generate. The examples and labels are input to the model for purposes of training the model and an algorithm is used to "learn" the correct behavior. When trained (i.e., the weights connecting neurons have converged and become stable or within an acceptable amount of variation), the model will operate to respond to an input sample of data to generate a correct response or decision.

Any of the software components, processes or functions described in this application may be implemented as software code to be executed by a processor using any suitable computer language such as Python, Java, JavaScript, C, C++, or Perl using conventional or object-oriented techniques. The software code may be stored as a series of instructions, or commands in (or on) a non-transitory computer-readable medium, such as a random-access memory (RAM), a read only memory (ROM), a magnetic medium such as a hard-drive or a floppy disk, or an optical medium such as a CD-ROM. In this context, a non-transitory computer-readable medium is almost any medium suitable for the storage of data or an instruction set aside from a transitory waveform. Any such computer readable medium may reside on or within a single computational apparatus and may be present on or within different computational apparatuses within a system or network.

According to one example implementation, the term processing element or processor, as used herein, may be a central processing unit (CPU), or conceptualized as a CPU (such as a virtual machine). In this example implementation, the CPU or a device in which the CPU is incorporated may be coupled, connected, and/or in communication with one or more peripheral devices, such as display. In another example implementation, the processing element or processor may be incorporated into a mobile computing device, such as a smartphone or tablet computer.

The non-transitory computer-readable storage medium referred to herein may include a number of physical drive units, such as a redundant array of independent disks (RAID), a floppy disk drive, a flash memory, a USB flash drive, an external hard disk drive, thumb drive, pen drive, key drive, a High-Density Digital Versatile Disc (HD-DV D) optical disc drive, an internal hard disk drive, a Blu-Ray optical disc drive, or a Holographic Digital Data Storage (HDDS) optical disc drive, synchronous dynamic random access memory (SDRAM), or similar devices or other forms of memories based on similar technologies. Such computer-readable storage media allow the processing element or processor to access computer-executable process steps, application programs and the like, stored on removable and non-removable memory media, to off-load data from a device or to upload data to a device. As mentioned, with regards to the embodiments described herein, a non-transitory computer-readable medium may include almost any structure, technology, or method apart from a transitory waveform or similar medium.

Certain implementations of the disclosed technology are described herein with reference to block diagrams of systems, and/or to flowcharts or flow diagrams of functions, operations, processes, or methods. It will be understood that one or more blocks of the block diagrams, or one or more stages or steps of the flowcharts or flow diagrams, and combinations of blocks in the block diagrams and stages or steps of the flowcharts or flow diagrams, respectively, can be implemented by computer-executable program instructions. Note that in some embodiments, one or more of the blocks, or stages or steps may not necessarily need to be performed in the order presented or may not necessarily need to be performed at all.

These computer-executable program instructions may be loaded onto a general-purpose computer, a special purpose computer, a processor, or other programmable data processing apparatus to produce a specific example of a machine, such that the instructions that are executed by the computer, processor, or other programmable data processing apparatus create means for implementing one or more of the functions, operations, processes, or methods described herein. These computer program instructions may also be stored in a computer-readable memory that can direct a computer or other programmable data processing apparatus to function in a specific manner, such that the instructions stored in the computer-readable memory produce an article of manufacture including instruction means that implement one or more of the functions, operations, processes, or methods described herein.

While certain implementations of the disclosed technology have been described in connection with what is presently considered to be the most practical and various implementations, it is to be understood that the disclosed technology is not to be limited to the disclosed implementations. Instead, the disclosed implementations are intended to cover various modifications and equivalent arrangements included within the scope of the appended claims. Although specific terms are employed herein, they are used in a generic and descriptive sense only and not for purposes of limitation.

This written description uses examples to disclose certain implementations of the disclosed technology, and to enable any person skilled in the art to practice certain implementations of the disclosed technology, including making and using any devices or systems and performing any incorporated methods. The patentable scope of certain implementations of the disclosed technology is defined in the claims, and may include other examples that occur to those skilled in the art. Such other examples are intended to be within the scope of the claims if they have structural and/or functional elements that do not differ from the literal language of the claims, or if they include structural and/or functional elements with insubstantial differences from the literal language of the claims.

All references, including publications, patent applications, and patents, cited herein are hereby incorporated by reference to the same extent as if each reference were individually and specifically indicated to be incorporated by reference and/or were set forth in its entirety herein.

The use of the terms "a" and "an" and "the" and similar referents in the specification and in the following claims are to be construed to cover both the singular and the plural, unless otherwise indicated herein or clearly contradicted by context. The terms "having," "including," "containing" and similar referents in the specification and in the following claims are to be construed as open-ended terms (e.g., meaning "including, but not limited to,") unless otherwise noted. Recitation of ranges of values herein are merely indented to serve as a shorthand method of referring individually to each separate value inclusively falling within the range, unless otherwise indicated herein, and each separate value is incorporated into the specification as if it were individually recited herein. All methods described herein can be performed in any suitable order unless otherwise indicated herein or clearly contradicted by context. The use of any and all examples, or exemplary language (e.g., "such as") provided herein, is intended merely to better illuminate embodiments of the invention and does not pose a limitation to the scope of the invention unless otherwise claimed. No language in the specification should be construed as indicating any non-claimed element as essential to each embodiment of the present invention.

As used herein (i.e., the claims, figures, and specification), the term "or" is used inclusively to refer items in the alternative and in combination.

Different arrangements of the components depicted in the drawings or described above, as well as components and steps not shown or described are possible. Similarly, some features and sub-combinations are useful and may be employed without reference to other features and sub-combinations. Embodiments of the invention have been described for illustrative and not restrictive purposes, and alternative embodiments will become apparent to readers of this patent. Accordingly, the present invention is not limited to the embodiments described above or depicted in the drawings, and various embodiments and modifications can be made without departing from the scope of the claims below.

That which is claimed is:

1. A method of treating a patient, comprising:
determining by a processor, a current state of a medical condition of a patient;
determining by the processor, a likelihood of the patient entering a more severe state of the medical condition than the current state, wherein the determining of the likelihood of the patient entering a more severe state of the medical condition further comprises:
acquiring by the processor data characterizing the current state of the medical condition of the patient, the acquired data including at least two different types or sources of data, the types or sources of data including one or more of an X-Ray or data store for X-Rays, an MRI or data store for MRIs, an EKG or data store for EKGs, an ultrasound or data store for ultrasound data, or a lab result or a data store for lab results;
for each different type or source of data, using the processor to apply at least one of a plurality of machine learning models by inputting the data characterizing the current state of the medical condition of the patient;
generating by the processor an output metric for each of the plurality of applied machine learning models;
combining, by the processor, the output metric of each of the plurality of applied machine learning models into a composite metric, wherein the composite metric represents the likelihood of the patient condition entering the more severe state of the medical condition, wherein the composite metric is generated by forming a weighted combination of the output metric of each of the plurality of applied machine learning models, wherein one or more weights in the weighted combination are a function of an amount of time since the current state of the medical condition of the patient was determined;
in response to determining the composite metric, the processor automatically initiating a request for a specific process, resource, test, follow-up procedure, or additional assistance, wherein the request is for one or more of an increase of supplemental oxygen, application of an additional therapy, noninvasive ventilation, ventilation, prone positioning of the patient, or Extracorporeal Membrane Oxygenation (ECMO) prior to the patient entering a more severe state of the medical condition and thereby more efficiently allocating resources within a clinical setting;

receiving the requested process, resource, test, follow-up procedure, or additional assistance from a resource within the clinical setting; and administering or treating the patient with one or more of an increase of supplemental oxygen, the additional requested therapy, a form of ventilation, an adjustment to the positioning of the patient, or application of Extracorporeal Membrane Oxygenation (ECMO) prior to the patient entering a more severe state of the medical condition.

2. The method of claim 1, wherein the acquired data comprises two or more of lab results, x-rays, ultrasound images, lung images, waveforms indicating a state of the patient's organs or body functions, clinical observations, and psychological profile information.

3. The method of claim 1, wherein the medical condition is a viral infection, and further, wherein the viral infection is a coronavirus.

4. The method of claim 1, further comprising receiving a selection of one of one or more selectable resources, tests, follow-up procedures, or requests for additional assistance, wherein the resource is an item of medical equipment, a staff member, a trained operator, a doctor, a nurse, a hospital bed, or other aspect of a hospital's capacity to treat patients.

5. The method of claim 1, further comprising the processor generating a user interface display on a device, wherein the generated user interface display includes a recommended treatment approach based on both the composite metric and a threshold value or range for the composite metric selected by a clinical professional or other medical service provider.

6. The method of claim 1, further comprising:

the processor accessing information describing a level of a resource expected to be needed to treat the patient when the medical condition of the patient enters the more severe state; and the processor generating a display of the composite metric and the accessed information describing the level of the resource expected to be needed on a device viewable by a clinical professional.

7. The method of claim 6, further comprising receiving an instruction from the clinical professional to alter a current level of the resource to the level of the resource expected to be needed to treat the patient when the medical condition of the patient enters the more severe state.

8. The method of claim 1, wherein each of the plurality of machine learning models is trained by a process comprising:

identifying a type of medical data associated with progression of a disease or illness;

acquiring examples of the identified type of medical data for a set of patients;

separating the acquired examples of the medical data into a first group indicative of a specific stage of the disease or illness and a second group that is not indicative of the specific stage of the disease or illness; and training the model using each group of data and an associated label, wherein the associated label indicates whether the group of data is indicative or is not indicative of the specific stage of the disease or illness.

9. The method of claim 1, wherein the more severe state of the medical condition indicated by the composite metric is Acute Respiratory Distress Syndrome (ARDS).

10. A system for treating a patient, comprising:

one or more electronic processors configured to execute a set of computer-executable instructions;

one or more non-transitory electronic data storage media containing the set of computer-executable instructions, wherein when executed, the instructions cause the one or more electronic processors to:

determine a current state of a medical condition of a patient;

determine a likelihood of the patient entering a more severe state of the medical condition than the current state, wherein determining the likelihood of the patient entering a more severe state of the medical condition further comprises;

acquiring data characterizing the current state of the medical condition of the patient, the acquired data including at least two different types or sources of data, the types or sources of data including one or more of an X-Ray or data store for X-Rays, an MRI or data store for MRIs, an EKG or data store for EKGs, an ultrasound or data store for ultrasound data, or a lab result or a data store for lab results;

for each different type or source of data, applying at least one of a plurality of machine learning models by inputting the data characterizing the current state of the medical condition of the patient;

generating an output metric for each of the plurality of applied machine learning models;

combining the output metric of each of the plurality of applied machine learning models into a composite metric, wherein the composite metric represents the likelihood of the patient condition entering the more severe state of the medical condition, wherein the composite metric is generated by forming a weighted combination of the output metric of each of the plurality of applied machine learning models, wherein one or more weights in the weighted combination are a function of an amount of time since the current state of the medical condition of the patient was determined;

in response to determining the composite metric, automatically initiating a request for a specific process, resource, test, follow-up procedure, or additional assistance, wherein the request is for one or more of an increase of supplemental oxygen, application of an additional therapy, noninvasive ventilation, ventilation, prone positioning of the patient, or Extracorporeal Membrane Oxygenation (ECMO) prior to the patient entering a more severe state of the medical condition and thereby more efficiently allocating resources within a clinical setting;

determine that the requested process, resource, test, follow-up procedure, or additional assistance has been received from a resource within the clinical setting; and determine that the patient has had administered or been treated with one or more of an increase of supplemental oxygen, the additional requested therapy, a form of ventilation, an adjustment to the positioning of the patient, or application of Extracorporeal Membrane Oxygenation (ECMO) prior to the patient entering a more severe state of the medical condition.

11. The system of claim 10, wherein the acquired data comprises two or more of lab results, X-rays, ultrasound images, waveforms or signals indicating a state of the patient's organs or body functions, clinical observations, and psychological profile information.

12. The system of claim 10, wherein the medical condition is a viral infection, and further, wherein the viral infection is a coronavirus.

13. The system of claim 10, wherein the instructions further cause the one or more processors to receive a selection of one of one or more selectable resources, tests, follow-up procedures, or requests for additional assistance, wherein the resource is an item of medical equipment, a staff member, a trained operator, a doctor, a nurse, a hospital bed, or other aspect of a hospital's capacity to treat patients.

14. The system of claim 10, wherein the instructions further cause the one or more processors to generate a user interface display on a device, wherein the generated user interface display includes a recommended treatment approach based on both the composite metric and a threshold value or range for the composite metric selected by a clinical professional or other medical service provider.

15. The system of claim 10, wherein the instructions further cause the one or more electronic processors to:

access information describing a level of a resource expected to be needed to treat the patient when the medical condition of the patient enters the more severe state; and generate a display of the composite metric and the accessed information describing the level of the resource expected to be needed on a device viewable by a clinical professional.

16. The system of claim 15, wherein the instructions further cause the one or more electronic processors to receive an instruction from the clinical professional to alter a current level of the resource to the level of the resource expected to be needed to treat the patient when the medical condition of the patient enters the more severe state.

17. One or more non-transitory computer-readable media comprising a set of computer-executable instructions that when executed by one or more programmed electronic processors, cause a patient to be treated by:

determining a current state of a medical condition of a patient;

determining a likelihood of the patient entering a more severe state of the medical condition than the current state, wherein determining the likelihood of the patient entering a more severe state of the medical condition further comprises;

acquiring data characterizing the current state of the medical condition of the patient, the acquired data including at least two different types or sources of data, the types or sources of data including one or more of an X-Ray or data store for X-Rays, an MRI or data store for MRIs, an EKG or data store for EKGs, an ultrasound or data store for ultrasound data, or a lab result or a data store for lab results;

for each different type or source of data, applying at least one of a plurality of machine learning models by inputting the data characterizing the current state of the medical condition of the patient;

generating an output metric for each of the plurality of applied machine learning models;

combining the output metric of each of the plurality of applied machine learning models into a composite metric, wherein the composite metric represents the likelihood of the patient condition entering the more severe state of the medical condition, wherein the composite metric is generated by forming a weighted combination of the output metric of each of the plurality of applied machine learning models, wherein one or more weights in the weighted combination are a function of an amount of time since the current state of the medical condition of the patient was determined;

in response to determining the composite metric, automatically initiating a request for a specific process, resource, test, follow-up procedure, or additional assistance, wherein the request is for one or more of an increase of supplemental oxygen, application of an additional therapy, noninvasive ventilation, ventilation, prone positioning of the patient, or Extracorporeal Membrane Oxygenation (ECMO) prior to the patient entering a more severe state of the medical condition and thereby more efficiently allocating resources within a clinical setting;

determining that the requested process, resource, test, follow-up procedure, of additional assistance has been received from a resource within the clinical setting; and determining that the patient has had administered or been treated with one or more of an increase of supplemental oxygen, the additional requested therapy, a form of ventilation, an adjustment to the positioning of the patient, or application of Extracorporeal Membrane Oxygenation (ECMO) prior to the patient entering a more severe state of the medical condition.

18. The one or more non-transitory computer-readable media of claim 17, wherein the acquired data comprises two or more of lab results, X-rays, ultrasound images, waveforms or signals indicating a state of the patient's organs or body functions, clinical observations, and psychological profile information, and wherein the instructions cause the one or more programmed electronic processors to receive a request for a resource, wherein the resource is an item of medical equipment, a staff member, a trained operator, a doctor, a nurse, a hospital bed, or other aspect of a hospital's capacity to treat patients.

* * * * *